United States Patent
Hong et al.

(10) Patent No.: US 8,167,940 B2
(45) Date of Patent: May 1, 2012

(54) ASPHERIC TORIC INTRAOCULAR LENS

(75) Inventors: Xin Hong, Fort Worth, TX (US); James Hoffman, Garland, TX (US); Jihong Xie, Jacksonville, FL (US); Michael Hamlin, Bedford, TX (US)

(73) Assignee: Novartis AG, Basel (CH)

( * ) Notice: Subject to any disclaimer, the term of this patent is extended or adjusted under 35 U.S.C. 154(b) by 271 days.

(21) Appl. No.: 12/435,241

(22) Filed: May 4, 2009

(65) Prior Publication Data
US 2009/0279048 A1    Nov. 12, 2009

Related U.S. Application Data

(60) Provisional application No. 61/050,911, filed on May 6, 2008.

(51) Int. Cl.
*A61F 2/16* (2006.01)
(52) U.S. Cl. ........................... 623/6.18; 623/6.23
(58) Field of Classification Search ............ 623/6.23, 623/6.18, 6.27–6.28
See application file for complete search history.

(56) References Cited

U.S. PATENT DOCUMENTS

| | | | |
|---|---|---|---|
| 5,796,462 A | 8/1998 | Roffman et al. | |
| 6,409,339 B1 * | 6/2002 | Wanders | 351/161 |
| 6,923,540 B2 * | 8/2005 | Ye et al. | 351/161 |
| 2003/0109926 A1 * | 6/2003 | Portney | 623/6.37 |
| 2004/0042073 A1 * | 3/2004 | Pynson | 359/367 |
| 2004/0068317 A1 | 4/2004 | Knight | |

FOREIGN PATENT DOCUMENTS

| | | |
|---|---|---|
| DE | 10 2005 028933 | 12/2006 |
| EP | 1 857 077 | 11/2007 |
| WO | WO 2004/010904 | 2/2004 |
| WO | WO 2006/060477 | 6/2006 |

OTHER PUBLICATIONS

International Search Report for PCT/US2009/042859, Publication No. WO2009/137491, 5 pages.
International Search Report for PCT/US2009/042859, Publication No. WO2009/137491, 5 pages.

* cited by examiner

*Primary Examiner* — William H. Matthews
(74) *Attorney, Agent, or Firm* — Jonathan E. Prejean

(57) ABSTRACT

An aspheric toric intraocular lens (IOL) having toricity and asphericity in a single lens. The toricity and asphericity may be provided on separate surfaces, such as an anterior surface and a posterior surface, or the toricity and asphericity may be combined onto a single surface. The edge thickness may be varied sinusoidal to maintain equal edge thickness at 45 degree meridian.

15 Claims, 20 Drawing Sheets

$$y = 0.21 + 0.015 * \cos((2*PI/180)*x)$$

$y = 0.21 + 0.015 * \cos((2*PI/180)*x)$

ASPHERIC TORIC INTRAOCULAR LENS

RELATED APPLICATIONS

This application claims priority to U.S. provisional application Ser. No. 61/050,911, filed on May 6, 2008, the contents which are incorporated herein by reference.

TECHNICAL FIELD

Embodiments of the present disclosure relate generally to intraocular lenses and, more particularly, to intraocular lenses combining asphericity and toricity.

BACKGROUND

Intraocular lenses (IOLs) are routinely implanted in patients' eyes during cataract surgery to replace the natural crystalline lens or to compensate for the lost optical power. The terms "intraocular lens" and its abbreviation IOL are used interchangeably herein to describe lenses that are implanted into the interior of an eye to either replace the natural lens or to otherwise augment vision regardless of whether or not the natural lens is removed.

Traditional IOLs are spherical, meaning the posterior surface is curved. However, aspheric IOLs have an aspheric surface to correct corneal spherical aberration. Toric IOLs have a toric surface to correct or mitigate corneal astigmatism over a range of diopters.

SUMMARY

Hence, there is a need for enhanced methods and ophthalmic lenses for correcting vision, and more particularly, for such methods and lenses that can be employed to compensate for the lost optical power of a removed natural lens. Thus, a need exists to improve the ability to restore vision across a range of object distances with out sacrificing any part of that range.

The terms "aspherical base curve" and "aspherical profile" are used herein interchangeably, and are well known to those skilled in the art. To the extent that any further explanation may be required, these terms are employed herein to refer to a radial profile of a surface that exhibits deviations from a spherical surface. Such deviations can be characterized, for example, as smoothly varying differences between the aspherical profile and a putative spherical profile that substantially coincides with the aspherical profile at the small radial distances from the apex of the profile. Further, the terms "substantially identical IOL" or "substantially identical lens," as used herein refer to an IOL that is formed of the same material as an aspherical IOL to which it is compared. Each surface of the "substantially identical IOL" has the same central radius (i.e., radius at the apex of the surface corresponding to the intersection of an optical axis with the surface) as that of the corresponding surface of the aspherical IOL. In addition, the "substantially identical IOL" has the same central thickness as the aspherical IOL to which it is compared. However, "substantially identical IOL" has spherical surface profiles; i.e., it lacks the asphericity exhibited by the aspherical IOL.

Embodiments of the present disclosure provide systems and methods of providing excellent vision across a range of object distances that eliminate, or at least substantially reduce, the shortcomings of prior art methods for improving vision.

Various embodiments provide IOLs which include both toricity and asphericity to correct or mitigate corneal astigmatism and spherical aberrations. The toricity and asphericity may be on two separate surfaces or may be present on a single surface. A single asphericity may be presented for all cylinder meridians or a variable asphericity may be presented for different meridians. For examples, different degrees of asphericity may be used for the two primary meridians of the astigmatism. Embodiments disclosed herein may be useful for correcting or mitigating other aberrations, such as coma, trefoil, tetrafoil, and the like. Higher order aberrations may also be possible.

Lenses that provided toricity and asphericity either on separate surfaces or on combined surfaces had excellent toricity and spherical aberration, and the lens quality and resolution efficiency exceeded 4/6. Embodiments disclosed herein may also be manufactured using existing processes.

One embodiment of an aspheric toric lens can be included in an ophthalmic device, comprising an ophthalmic lens having an anterior surface and a posterior surface and one or more haptics coupled to the ophthalmic lens. One of the posterior or anterior surfaces is shaped so that the ophthalmic lens is configured as an aspheric lens and one of the posterior or anterior surfaces is shaped so that the ophthalmic lens is configured as a toric lens. For example, the posterior surface can be shaped so that the ophthalmic lens is configured as an aspheric lens and the anterior surface shaped so that the ophthalmic lens is configured as a toric lens. Or, the anterior surface can be shaped so that the ophthalmic lens is configured as an aspheric lens and the posterior surface shaped so that the ophthalmic lens is configured as a toric lens.

In one embodiment, an aspheric toric intraocular lens with toricity and asphericity on separate surfaces may be described analytically as:

$$sag_1 = toric(r, \theta)$$
$$sag_2 = asph(r)$$
$$toric(r, \theta) = \frac{(c_x\cos^2\theta + c_y\sin^2\theta)r^2}{1 + \sqrt{1 - (1+k_x x)c_x^2 r^2 \cos^2\theta - (1+k_y)c_y^2 r^2 \sin^2\theta}},$$
$$c_x = \frac{1}{R_{1x}},$$
$$c_y = \frac{1}{R_{1y}}$$
$$asph(r) = \frac{cr^2}{1 + \sqrt{1 - (1+k)c^2 r^2}},$$
$$c = \frac{1}{R_2}$$

where, r, θ are the axial distance from lens center and the meridian angle. The $c_x$, $c_y$, and $k_x$, $k_y$ are the curvatures and conic constants for two toric principal meridians. In this embodiment, $k_x$ and $k_y$ are preferably equal to zero.

In the above examples, separate surfaces are shaped to provide asphericity and toricity. In other embodiments, a single surface may be shaped to provide these features. For example, the posterior surface can be shaped so that the ophthalmic lens is configured as the aspheric lens and the toric lens. That is the posterior surface is shaped to provide both asphericity and toricity. According to another embodiment, the anterior surface can be shaped so that the ophthalmic lens is configured as the aspheric lens and the toric lens.

A lens with a particular surface shaped to provided toricity and asphericity can be described by:

$$sag_1 = \text{toric}(r, \theta)$$

$$\text{toric}(R_{avg}, r, \theta) = \frac{(c_x\cos^2\theta + c_y\sin^2\theta)r^2}{1 + \sqrt{1 - (1+k_k)c_x^2 r^2\cos^2\theta - (1+k_y)c_y^2 r^2\sin^2\theta}}$$

$$c_x = \frac{1}{R_x},$$

$$c_y = \frac{1}{R_y}$$

Preferably, ophthalmic devices disclosed herein have an optical power of 6 D-34 D. In a related embodiments, R is in a range of about 12 mm to about 120 mm (magnitude only, sign could be both positive and negative). In some embodiments, $c_x$ can be in a range of about 0.008 mm^-1 to about 0.08 mm^-1 (magnitude only, sign could be both positive and negative), $c_y$ can be in a range of about 0.008 mm^-1 to about 0.08 mm^-1 (magnitude only, sign could be both positive and negative), $k_x$ can be in a range of about −3000 to about −12, and $k_y$ can be in a range of about −3000 to about −12. Further, in some embodiments, the aspheric conic constant (k) can be in a range of about −3000 to about −12. Additionally c can be in a range of about 0.008 mm^-1 to about 0.08 mm^-1 (magnitude only, sign could be both positive and negative).

According to various embodiments, the ophthalmic lens has a selected edge thickness at the 45 degree meridian. The selected edge thickness can be any desired thickness, but is preferably in a range of 0.2 to 0.3 mm and preferably 0.21 mm at the 45 degree meridian. The edge thickness can be constant around the lens or can vary. For example, the edge thickness can vary periodically, such as sinusoidally. The center thickness of the lens can also be selected. Because the edge and center thickness of the lens can be selected, the lens can be shaped so that it can fit in and be implanted with existing surgical equipment, such as that used to implant the AcrySof IQ™ (AcrySof and AcrySof IQ are trademarks of Alcon Laboratories of Fort Worth, Tex.).

According to one embodiment of the ophthalmic device, the aspheric surface is shaped with the same asphericity for all meridians. Alternatively, the lens can be shaped with different asphericities for different meridians. For example, the lens can be shaped with a first asphericity for a first meridian and a second asphericity for a second meridian. The first and second meridians can be, by way of example, but not limitation, the principle meridians of astigmatism.

The ophthalmic device can include haptics configured to minimize movement of the ophthalmic device in the eye. The haptics can be made of biocompatible material such as AcrySof® (AcrySof™ is a trademark of Alcon Laboratories of Fort Worth, Tex.). The haptics can be roughened to promote adherence with biological material.

The lens can further include one or more markers to allow a surgeon to locate the lens relative to the principle meridians of the astigmatism. The markers can be small dots, raised portions or other feature that surgeon can see during surgery, but, preferably, the patient cannot discern after the procedure is complete.

Embodiments can further include ophthalmic methods. One embodiment of the ophthalmic method can include selecting an ophthalmic device as described herein and implanting the ophthalmic device in the eye of a patient. The ophthalmic device can be implanted using surgical procedures known to those of ordinary skill in the art and preferably using existing surgical tools. The ophthalmic device can be selected based on a variety of factors, including to minimize residual astigmatism in the eye as a whole, maintain a preoperative cylinder axis or to reduce residual astigmatism at selected meridians.

BRIEF DESCRIPTION OF THE FIGURES

A more complete understanding of the disclosure and the advantages thereof may be acquired by referring to the following description, taken in conjunction with the accompanying drawings in which like reference numbers generally indicate like features and wherein.

DETAILED DESCRIPTION

As used herein, the terms "comprises," "comprising," "includes," "including," "has," "having" or any other variation thereof, are intended to cover a non-exclusive inclusion. For example, a process, process, article, or apparatus that comprises a list of elements is not necessarily limited only to those elements but may include other elements not expressly listed or inherent to such process, process, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Additionally, any examples or illustrations given herein are not to be regarded in any way as restrictions on, limits to, or express definitions of, any term or terms with which they are utilized. Instead these examples or illustrations are to be regarded as being described with respect to one particular embodiment and as illustrative only. Those of ordinary skill in the art will appreciate that any term or terms with which these examples or illustrations are utilized will encompass other embodiments which may or may not be given therewith or elsewhere in the specification and all such embodiments are intended to be included within the scope of that term or terms. Language designating such nonlimiting examples and illustrations includes, but is not limited to: "for example," "for instance", "e.g.", "in one embodiment".

Various embodiments are illustrated in the FIGURES, like numerals being used to refer to like and corresponding parts of the various drawings.

Embodiments disclosed herein provide systems and methods for eliminating or mitigating corneal astigmatism and corneal spherical aberration.

Embodiments disclosed herein provide ophthalmic lenses that include at least one lens surface having an asphericity selected to correct or mitigate spherical aberrations contrast and at least one lens surface having a toricity selected to correct or mitigate astigmatism. Embodiments disclosed herein provide ophthalmic lenses that include at least one lens surface having an asphericity selected to improve image contrast relative to that provided by a substantially identical lens in which the respective surface is spherical. In the embodiments below, the embodiments are illustrated primarily in connection with intraocular lenses. It should, however, be understood that these teachings apply equally to a variety of other ophthalmic lenses, such as contact lenses.

Figure 1:
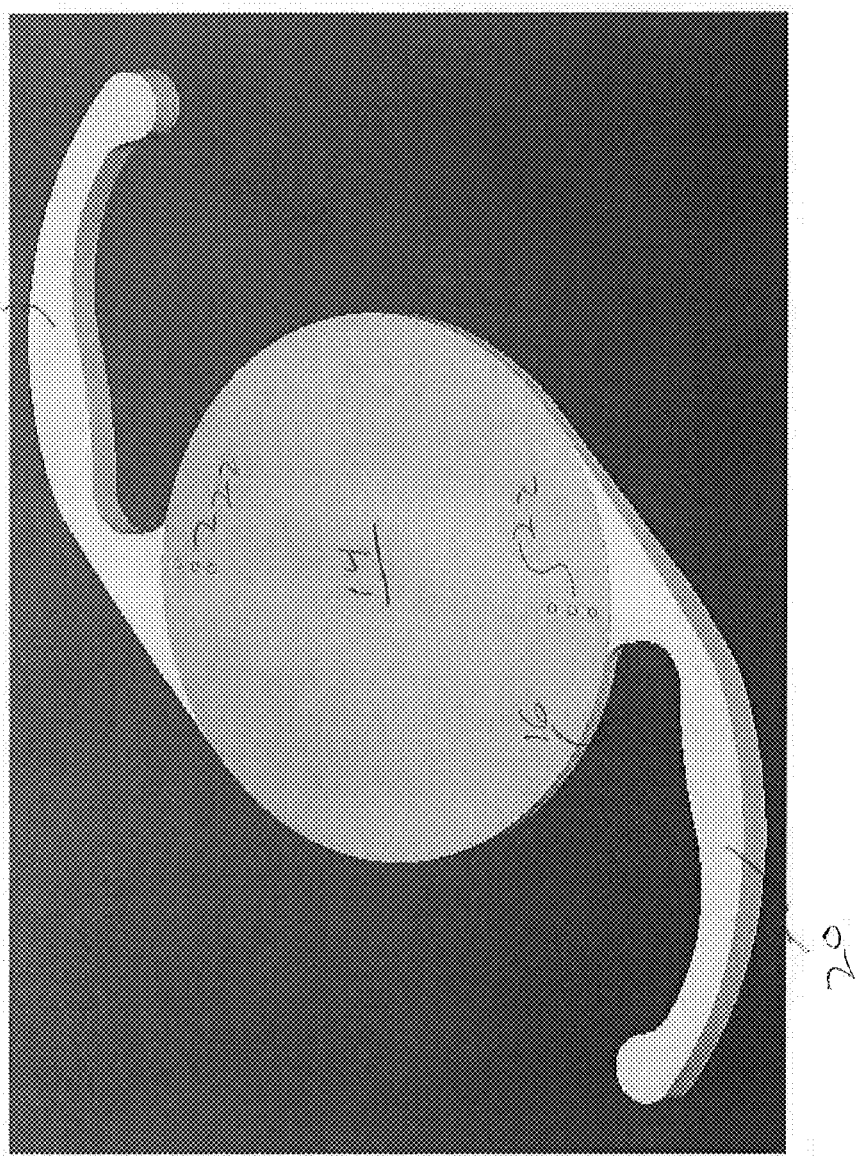
FIG. 1 schematically illustrates one embodiment of an aspheric toric intraocular lens 10 according to one design having toricity and asphericity on separated surfaces.

FIG. 1 depicts a perspective view of one embodiment of aspheric toric intraocular lens (IOL) 10. In some embodiments, lens 10 may include anterior surface 14, posterior surface 16 on the obverse side and markings 22. Aspheric toric IOL 10 may further include radially extending fixation members or haptics 20 for its placement in a patient's eye. Lens 10 can be formed of a biocompatible polymeric material, such as soft acrylic, silicone or hydrogel materials. In some embodiments, any biocompatible—preferably soft—material that exhibits a requisite index of refraction for a particular application of the lens can be employed. In some embodiments, a material manufactured under the trademark AcrySof™ (AcrySof is a trademark of Alcon Laboratories of Fort Worth, Tex.) may be used to form IOL 10. Further, the fixation members 20 can be also be formed of suitable polymeric materials, such as polymethyl methacrylate (PMMA), polypropylene and the like. Fabrication of intraocular lenses may include known fabrication processes such as pin cutting, wafer molding and lens casting.

Figure 2:
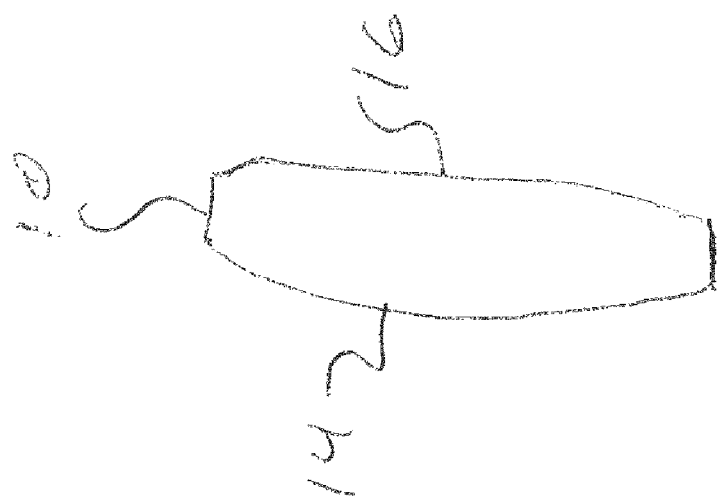
FIG. 2 schematically illustrate one embodiment of an aspheric toric intraocular lens 10 according to one design having toricity and asphericity on a separated surfaces.

FIG. 2 depicts one embodiment of an aspheric toric intraocular lens 10 according to one design having an anterior surface 14 and a posterior surface 16. As depicted in FIG. 2, in some embodiments, the toricity and asphericity of lens 10 may be present on different surfaces (i.e., a separated aspheric toric IOL 10, also referred to as a separated design lens 10). In some embodiments, separated design lens 10 may have an associated base power, such as 21 Diopters (D), a cylinder, such as 1.50 D., a spherical aberration correction, such as 0.2 microns, and may have a conic on the anterior surface and the cylinder on the posterior surface. In some embodiments, the anterior surface may have an associated radius, such as 19.613 mm, and a conic, such as −36.211. In some embodiments, the posterior surface may have a first radius (Rad X) and a second radius (Rad Y). As depicted in FIG. 2, Rad X may be −23.808 mm and Rad Y may be −20.447 mm. Lens 10 may have a center of thickness, such as 0.611 mm.

In one embodiment, an aspheric toric intraocular lens with toricity and asphericity on separate surfaces may be described analytically as:

$$sag_1 = toric(r, \theta) \quad \text{Equation 1}$$

$$sag_2 = asph(r) \quad \text{Equation 2}$$

$$toric(r, \theta) = \frac{(c_x \cos^2 + c_y \sin^2\theta) r^2}{1 + \sqrt{1 - (1 + k_x x) c_x^2 r^2 \cos^2\theta - (1 + k_y) c_y^2 r^2 \sin^2\theta}}, \quad \text{Equation 3}$$

$$c_x = \frac{1}{R_{1x}}, c_y = \frac{1}{R_{1y}}$$

$$asph(r) = \frac{cr^2}{1 + \sqrt{1 - (1 + k) c^2 r^2}}, c = \frac{1}{R_2} \quad \text{Equation 4}$$

In some embodiments, lens 10 can provide an optical power in a range of about 6 D to about 30 D, and an aspheric surface of lens 10 can be characterized with c ranging from about 0.0152 mm$^{-1}$ to about 0.0659 mm.sup.$^{-1}$, k ranging from about −1162 to about −19, a.sub.$_1$ ranging from about −0.00032 mm.sup.$^{-1}$ to about −0.00020 mm$^{-1}$, $a_2$ ranging from about −0.0000003 (−3×10$^{-7}$) mm$^{-3}$ to about −0.000053 (−5.3×10$^{-5}$) mm$^{-3}$, and $a_3$ ranging from about 0.0000082 (8.2×0.10$^{-6}$) mm$^{-5}$ to about 0.000153 (1.53×10$^{-4}$) mm$^{-5}$.

In some embodiments, lens 10 can provide an optical power in a range of about 16 D to about 25 D, and an aspheric surface of the lens can be characterized with c ranging from about 0.0369 (1/27.1) mm$^{-1}$ to about 0.0541 (1/18.5) mm.sup.$^{-1}$, k ranging from about −73 to about −27, $a_1$ ranging from about −0.000209 mm$^{-1}$ to about −0.000264 mm$^{-1}$, $a_2$ ranging from about −0.0000297 mm$^3$ to about −0.0000131 mm$^3$, and $a_3$ ranging from about 0.00000978 mm$^{-5}$ to about 0.00000846 mm$^{-5}$.

In other embodiments, R is in a range of about 12 mm to about 120 mm (magnitude only, sign could be both positive and negative). In some embodiments, $c_x$ can be in a range of about 0.008 mm^−1 to about 0.08 mm^−1 (magnitude only, sign could be both positive and negative), $c_y$ can be in a range of about 0.008 mm^−1 to about 0.08 mm^−1 (magnitude only, sign could be both positive and negative), $k_x$ can be in a range of about −3000 to about −12, and $k_y$ can be in a range of about −3000 to about −12. Further, in some embodiments, the aspheric conic constant (k) can be in a range of about −3000 to about −12. Additionally c can be in a range of about 0.008 mm^−1 to about 0.08 mm^−1 (magnitude only, sign could be both positive and negative).

In many embodiments, the aspheric profile of the anterior surface can be designed to provide the patient with an image contrast characterized by a modulation transfer function (MTF). As known to those having ordinary skill in the art, a measured or calculated modulation transfer function (MTF) associated with a lens can provide a quantitative measure of image contrast provided by that lens. In general, a contrast or modulation associated with an optical signal, e.g., a two-dimensional pattern of light intensity distribution emanated from or reflected by an object to be imaged or associated with the image of such an object, can be defined in accordance with the following relation:

$$\frac{I_{max} - I_{min}}{I_{max} + I_{min}} \qquad \text{Equation 5}$$

wherein $I_{max}$ and $I_{min}$ indicate, respectively, a maximum or a minimum intensity associated with the signal. Such a contrast can be calculated or measured for each spatial frequency present in the optical signal. An MTF of an imaging optical system, such as the combined IOL and the cornea, can then be defined as a ratio of a contrast associated with an image of an object formed by the optical system relative to a contrast associated with the object. As is known, the MTF associated with an optical system is not only dependent on the spatial frequencies of the intensity distribution of the light illuminating the system, but it can also be affected by other factors, such as the size of an illumination aperture, as well as by the wavelength of the illuminating light.

In some embodiments, such as the embodiment depicted in FIG. 2, the asphericity of lens 10 may provide an MTF of at least about 0.9 at the focus measured or calculated with monochromatic light having a wavelength of about 550 nm at a spatial frequency of 50 line pairs per millimeter and an aperture (e.g., pupil size) of 5.0 mm. In some embodiments, the asphericity of the anterior surface is selected so as to provide a patient in which aspheric toric IOL 10 is implanted with an image contrast characterized by a modulation transfer function (MTF) that is around 0.9, while maintaining a depth of field that is within an acceptable range. The MTF can be, for example, in a range of about 0.85 to about 0.93 for an aperture of about 5.0 mm. As direct measurements of MTF in a patient's eye can be complicated, in many embodiments the image enhancement provided by an aspheric IOL can be evaluated by calculating an MTF theoretically in a model eye exhibiting selected corneal and/or natural lens aberrations corresponding to an individual patient's eye or the eyes of a selected group of patients. The information needed to model a patient's cornea and/or natural lens can be obtained from measurements of waveform aberrations of the eye performed by employing known topographical methods.

For the embodiment depicted in FIG. 2, a residual aberration for the x and y axes may be approximately 0.0012 microns along a first meridian and −0.0037 microns along a second meridian, and Δ (delta) may be approximately 0.0049 microns. For a theoretical evaluation of one embodiment fabricated from PMMA in CrystalWave, lens 10 may have a lens power of 14.787 D (x) and 15.883 D (y), with a cylinder of 1.096 D. The spherical aberration may be −0.3223132 microns.

Figure 3:
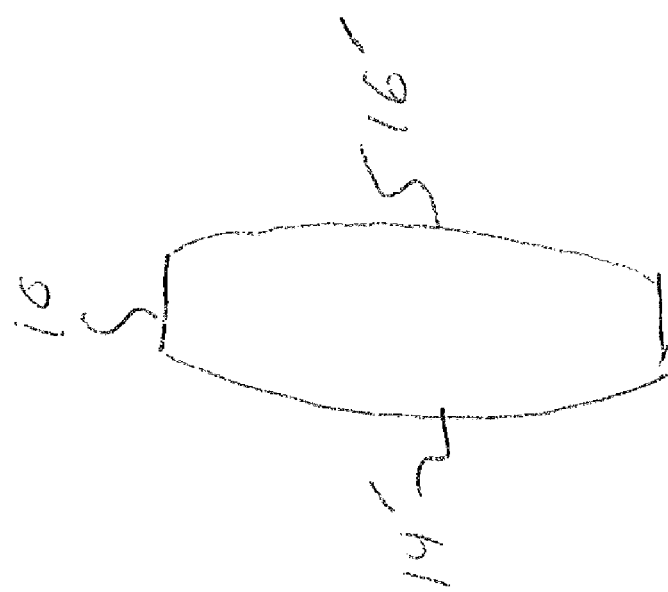
FIG. 3 schematically illustrates one embodiment of an aspheric toric intraocular lens 10 according to one design having toricity and asphericity on a single surface.
Figure 4:
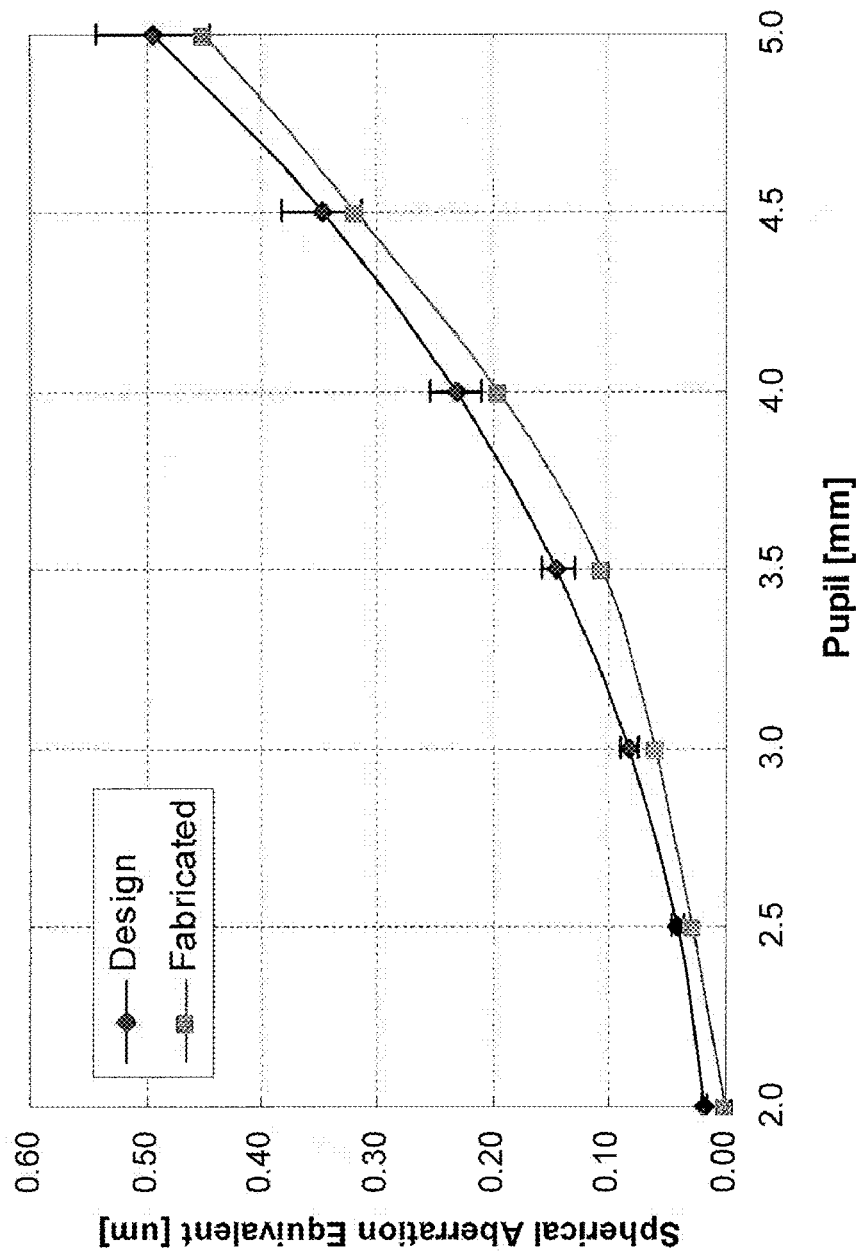
FIG. 4 depicts a graphical representation of the spherical aberration measurements for aspheric toric IOLs 10 using a separated design.

FIG. 3 schematically illustrates an aspheric toric intraocular lens 10 according to one embodiment. As depicted in FIG. 3, in some embodiments, the toricity and asphericity of an aspheric toric IOL 10 may be combined on the same surface (i.e., also referred to as a combined aspheric toric IOL 10). As depicted in FIG. 3, the toricity and asphericity may be combined on posterior surface 16'. In some embodiments, lens 10 may have a base power, such as 21 Diopters (D), a cylinder, such as 1.50 D, a spherical aberration correction, such as 0.2 microns, and may combine the conic and the cylinder on posterior surface 16'. In some embodiments, anterior surface 14' may have an associated radius, such as 19.609 mm. In some embodiments, posterior surface 16' may have a first radius (Rad X), a first conic (Conic X), a second radius (Rad Y), a second conic (Conic Y), an average radius (Rad avrg) and an average conic (Conic avrg). In FIG. 4, Rad X is approximately −23.814 mm, Conic X is approximately −65.571, Rad Y is approximately −20.451 mm, Conic Y is approximately −42.168, Rad avrg is approximately −22.005, and Conic avrg is approximately −51.953. Lens 10 may have a center of thickness, such as 0.612 mm and an edge thickness, such as 0.21 mm.

In one embodiment, a single surface with combined toricity and asphericity may be described analytically as $$sag_1 = \text{toric}(r, \theta) \qquad \text{Equation 6}$$

$$\text{toric}(R_{avg}, r, \theta) = \frac{(c_x \cos^2\theta + c_y \sin^2\theta)r^2}{1 + \sqrt{\begin{array}{c}1 - (1+k_k)c_x^2 r^2 \cos^2\theta - \\ (1+k_y)c_y^2 r^2 \sin^2\theta\end{array}}}, \qquad \text{Equation 7}$$

$$c_x = \frac{1}{R_x}, c_y = \frac{1}{R_y}$$

wherein for toric surfaces, $k_x$ and $k_y$ should not be zero.

$$\text{asph}(R_{avg}, r) = \frac{cr^2}{1 + \sqrt{1 - (1+k)c^2 r^2}}, c = \frac{1}{R_{avg}} \qquad \text{Equation 8}$$

In many embodiments, the aspheric profile of posterior surface 16' in a combined design can be designed to provide the patient with an image contrast characterized by a modulation transfer function (MTF) of at least about 0.9 at the focus measured or calculated with monochromatic light having a wavelength of about 550 nm at a spatial frequency of 50 line pairs per millimeter and an aperture (e.g., pupil size). The MTF can be, for example, in a range of about 0.85 to about 0.93 for an aperture of about 5.0 mm.

For the embodiment depicted in FIG. 3, a residual aberration for the x and y axes may be approximately 0.0039 microns along a first meridian and −0.0050 microns along a second meridian, and Δ (delta) may be approximately 0.0089 microns. For a theoretical evaluation of one embodiment fabricated from PMMA, lens 10 may have a lens power of 14.787 D (x) and 15.883 D (y), with a cylinder of 1.096 D. The spherical aberration may be −0.3099855 microns.

In some embodiments, better optics may be achieved by considering the amounts of lens toricity and asphericity as functions of pupil diameters (apertures). FIG. 4 depicts a graphical representation of the spherical aberration measurements for aspheric toric IOLs 10 using a separated design. In FIG. 4, the spherical aberration equivalent (in microns) for fabricated lenses 10a may be compared against the spherical aberration equivalent (in microns) for design lenses 10b at various pupil diameters ranging between 2.0 mm and 5.0 mm.

Figure 5:
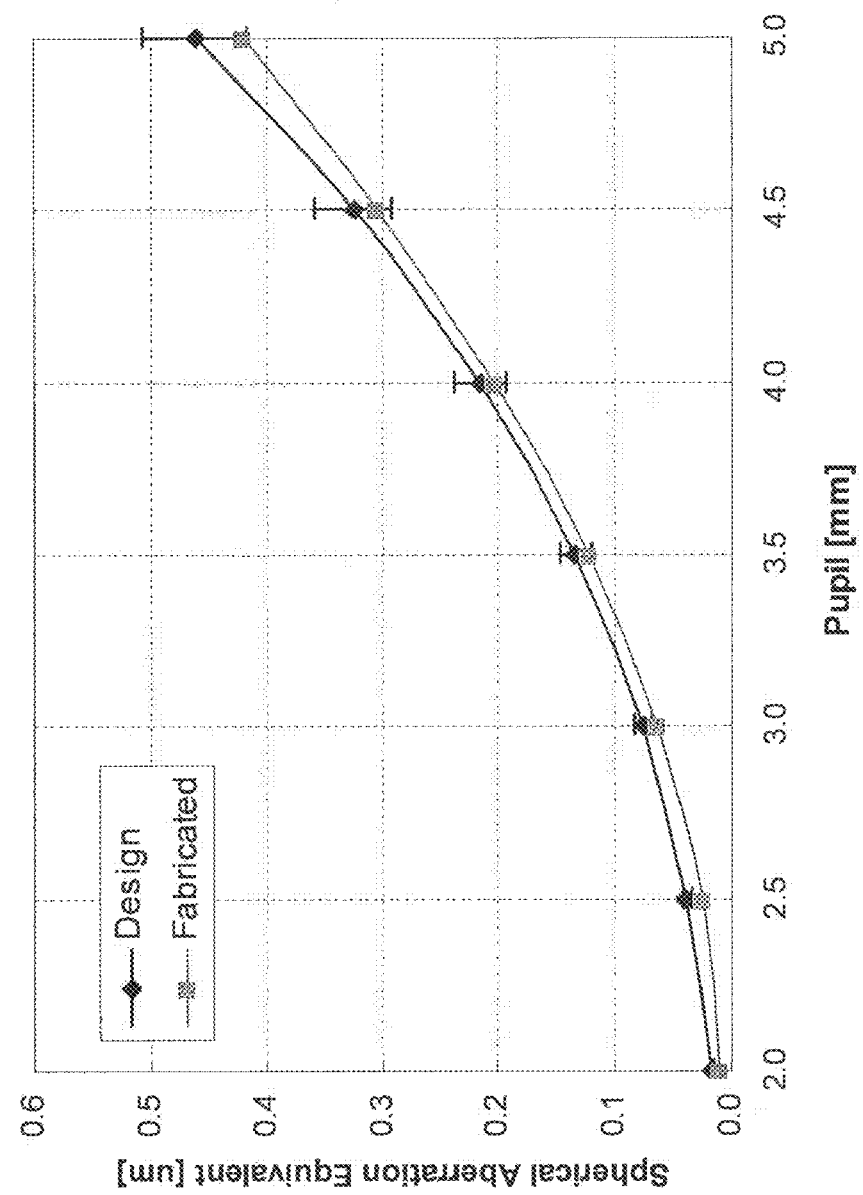
FIG. 5 depicts a graphical representation of the spherical aberration measurements for aspheric toric IOLs using a combined design.

FIG. 5 depicts a graphical representation of the spherical aberration measurements for aspheric toric IOLs 10 using a combined design. In FIG. 5, the spherical aberration equivalent (in microns) for fabricated lenses 10a may be compared against the spherical aberration equivalent (in microns) for design lenses 10b at various pupil diameters ranging between 2.0 mm and 5.0 mm.

Figure 6:
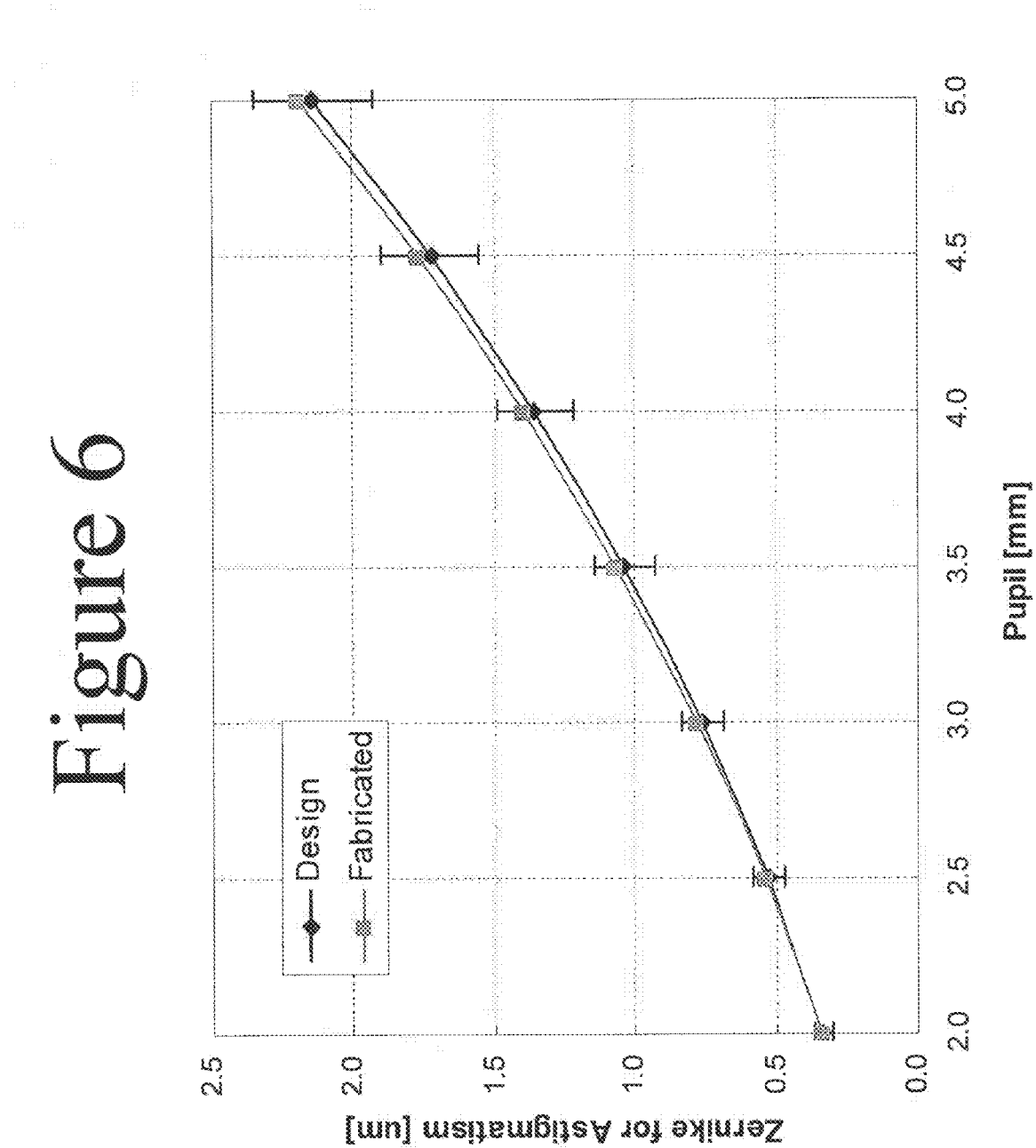
FIG. 6 depicts a graphical representation of the lens toricity measurements for aspheric toric IOLs using a separated design.

FIG. 6 depicts a graphical representation of the lens toricity measurements for aspheric toric IOLs 10 using a separated design. In FIG. 6, the Zernike coefficient for astigmatism (in microns) of fabricated lenses 10a may be compared against the Zernike coefficient for design lenses 10b at various pupil diameters ranging between 2.0 mm and 5.0 mm.

Figure 7:
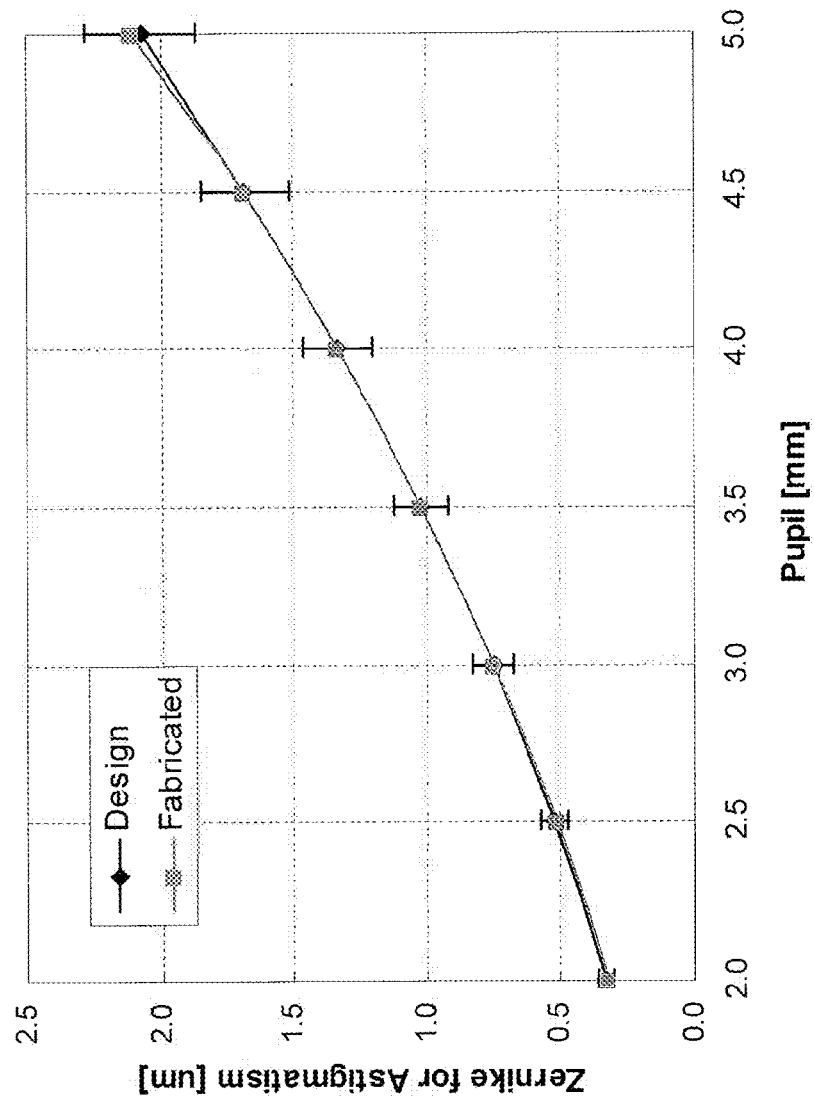
FIG. 7 depicts a graphical representation of the lens toricity measurements for aspheric toric IOLs using a combined design.

FIG. 7 depicts a graphical representation of the lens toricity measurements for aspheric toric IOLs 10 using a combined design. In FIG. 7, the Zernike coefficient for astigmatism (in microns) of fabricated lenses 10a may be compared against the Zernike coefficient for design lenses 10b at various pupil diameters ranging between 2.0 mm and 5.0 mm.

Figure 8:
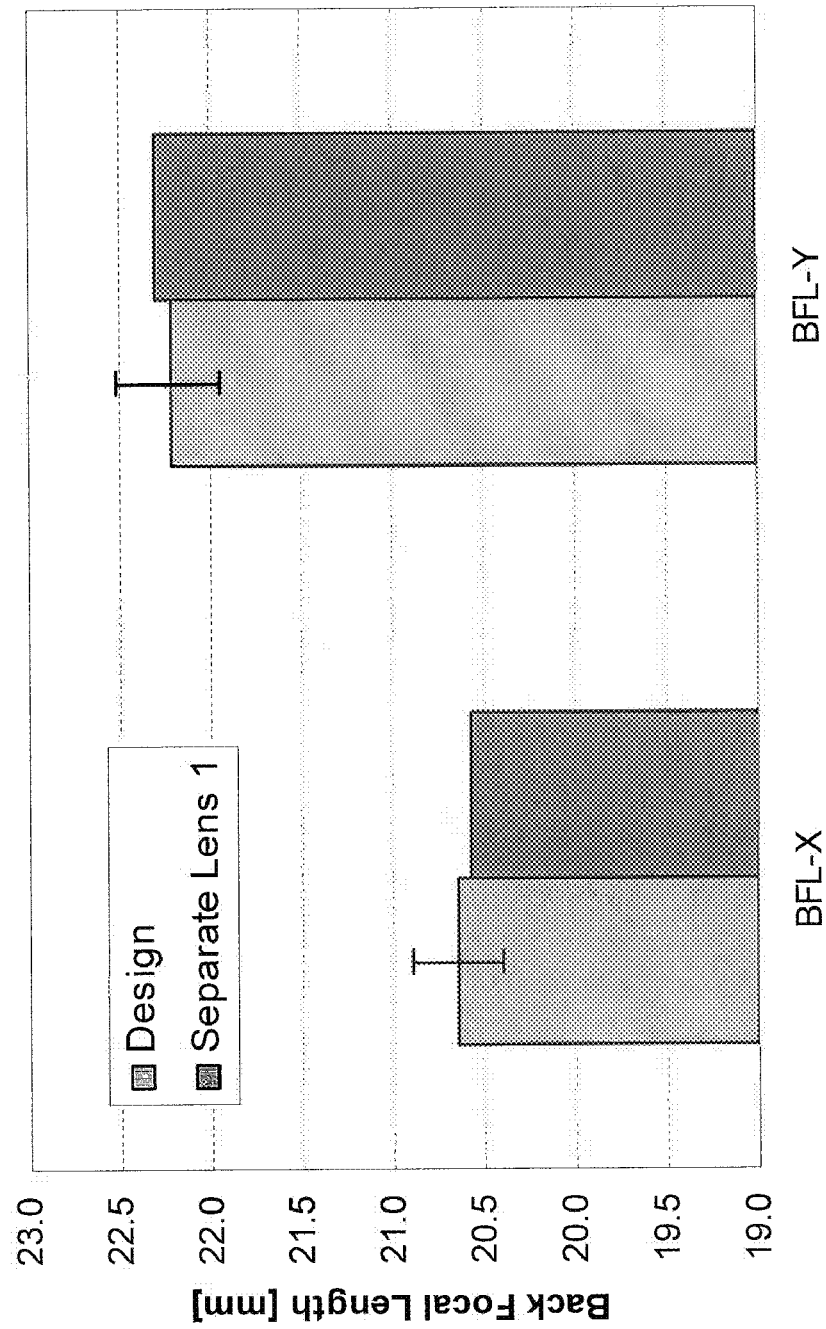
FIG. 8 depicts a graphical representation of the back focal length (BFL) measurements for aspheric toric IOLs using a separated design.

FIG. 8 depicts a graphical representation of the back focal length (BFL) measurements for aspheric toric IOLs 10 using a separated design and a combined design. In FIG. 8, the back focal length (in mm) may be compared between design lenses 10a and fabricated lenses 10b at BFL-X and BFL-Y. As depicted in FIG. 8, the BFL-X for the design lens 10a may be approximately 20.7 mm and the BFL-X for the separated lens 1-b may be approximately 20.60 mm.

Figure 9:
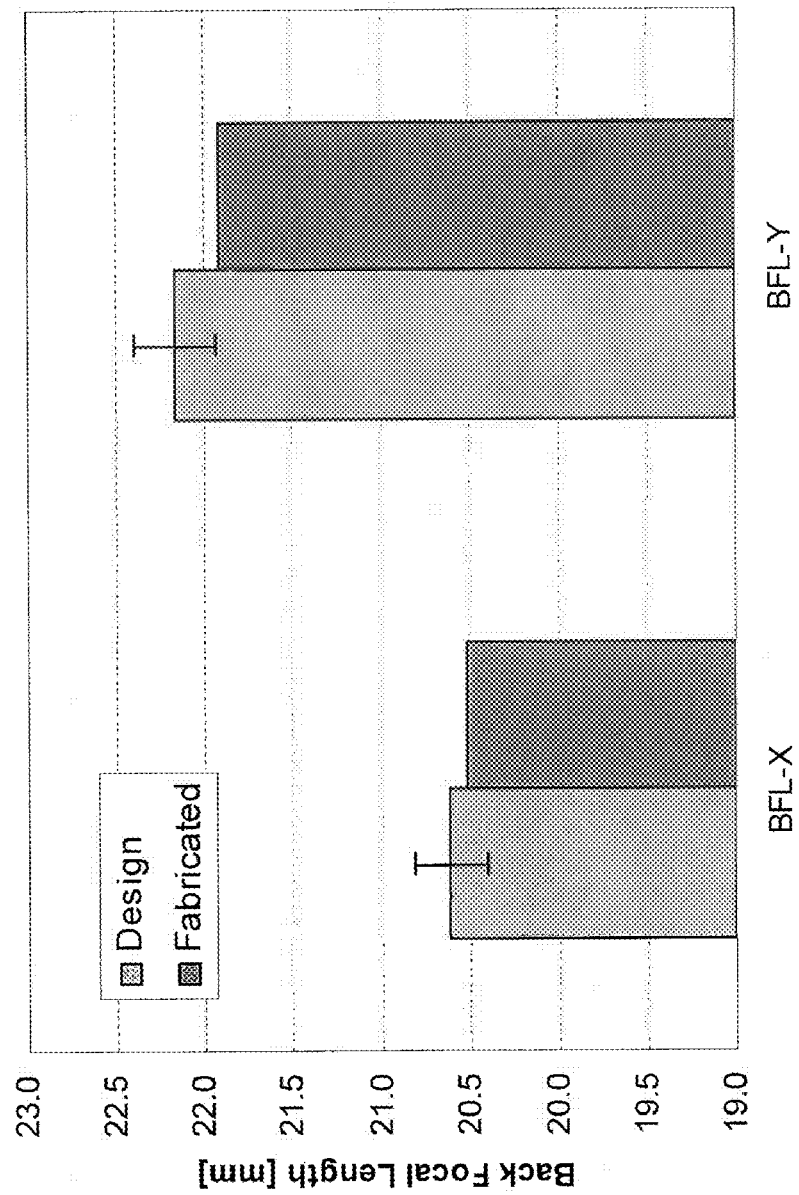
FIG. 9 depicts a graphical representation of the back focal length (BFL) measurements for aspheric toric IOLs using a combined design.

FIG. 9 depicts a graphical representation of the back focal length (BFL) measurements for aspheric toric IOLs 10 using a combined design. In FIG. 9, the back focal length (in mm) may be compared between design lenses 10a and fabricated lenses 10b at BFL-X and BFL-Y. As depicted in FIG. 9, the BFL-X for the design lens 10a may be approximately 20.7 mm and the BFL-X for the separated lens 10b may be approximately 20.10 mm.

Examples may be beneficial for pointing out advantages and features of the disclosure. Aspheric toric IOLs 10 may be fabricated from materials such as AcrySof® utilizing known fabrication processes. Fabrication processes may include, but are not limited to, pin cutting, wafer molding and lens casting. A toricity and asphericity may be provided on separate surfaces such as anterior surface 14 and posterior surface 16, or may be combined on a single surface, such as posterior surface 16'.

Figure 10:
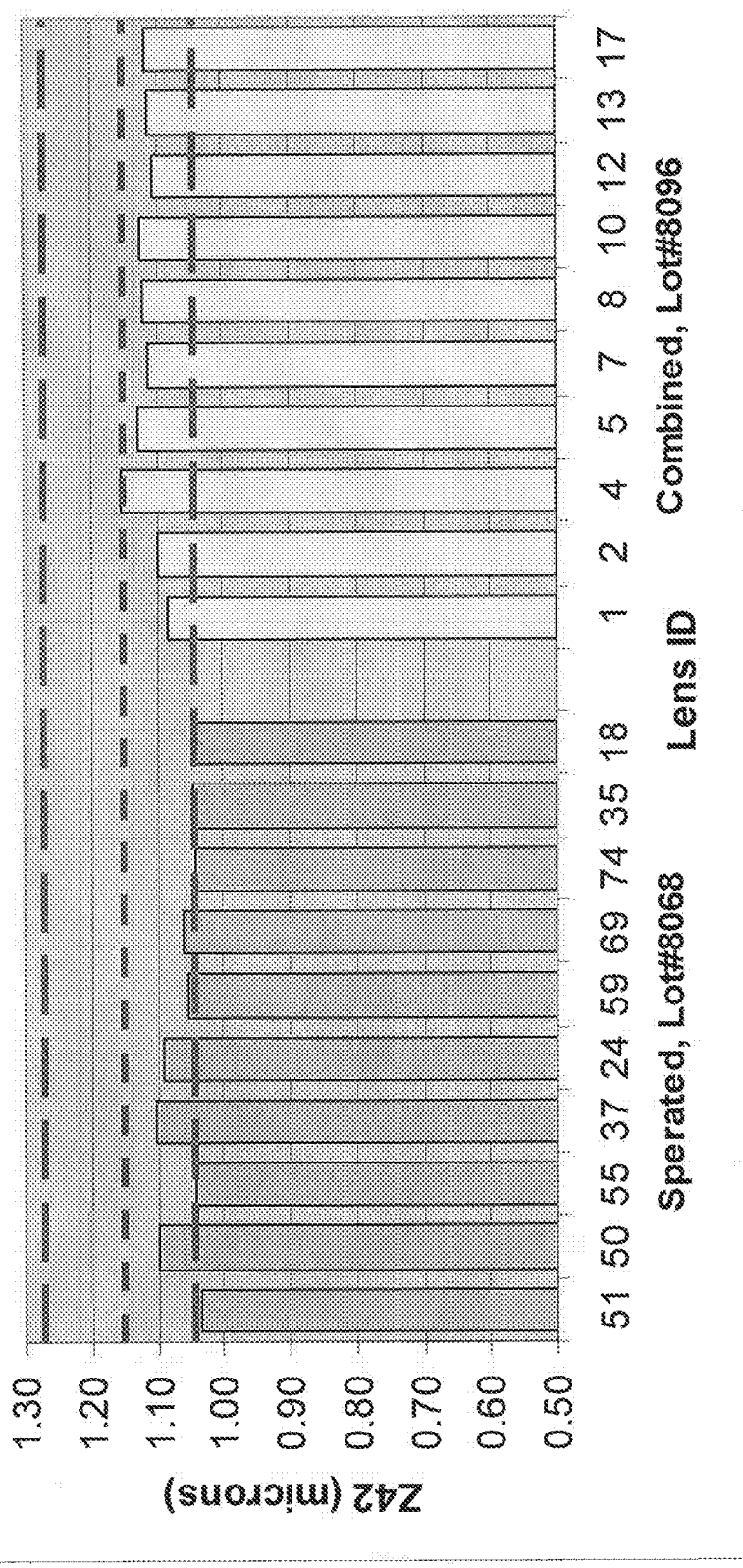
FIG. 10 is a graphical comparison of the lens toricity of ten separated design lenses 10 and ten combined design lenses for correction of a Z20 astigmatism.

FIG. 10 is a graphical comparison of the spherical aberration of ten separated design lenses 10 and ten combined design lenses 10 for correction of a Z42 spherical aberration at a 5.0 mm IOL aperture. FIG. 10 depicts the results of ten aspheric toric IOLs 10 having the toricity and asphericity on separate surfaces (i.e., anterior surface 14 and posterior surface 16) and ten aspheric toric IOLs 10 having the toricity and asphericity combined on a single surface (i.e., posterior surface 16'). Lenses 10 were taken from populations of product sets of approximately 100 lenses. Lenses 10 were tested against a spherical aberration Z42 at 5.0 mm IOL aperture. The results of the test provided a nominal correction of approximately 1.16 microns, with a minimum correction of approximately 1.05 microns and a maximum correction of approximately 1.28. In this test, the separated design had a correction at or below the nominal thickness, and five of the samples had a correction at or near the minimum correction. In this test, the combined design resulted in a correction below the nominal correction, and nine of the ten were at or above 1.10 microns.

Figure 11:
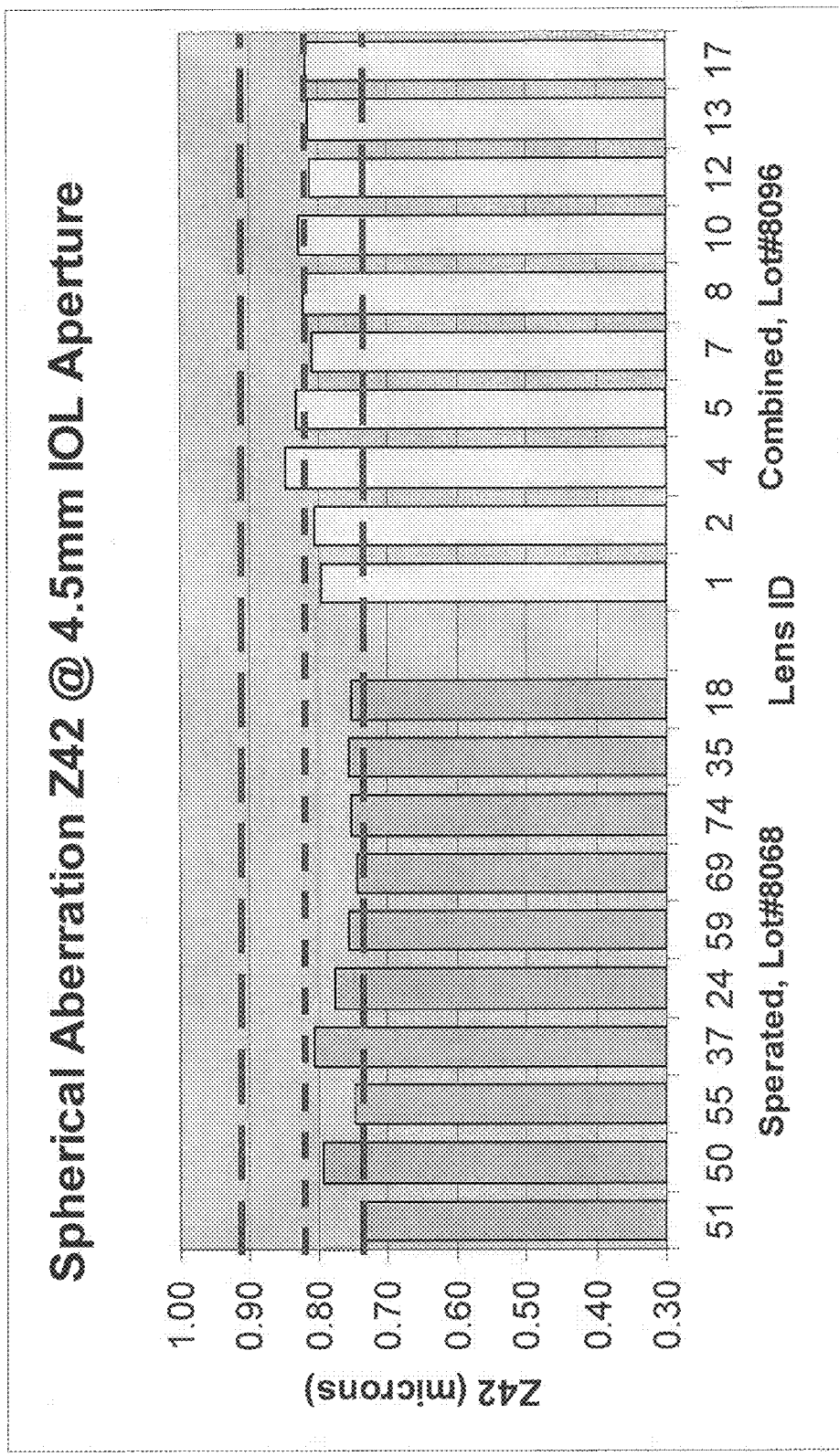
FIG. 11 is a graphical comparison of the spherical aberration of ten separated design lenses 10 and ten combined design lenses 10 for correction of a Z42 spherical aberration.

FIG. 11 is a graphical comparison of the spherical aberration of ten separated design lenses 10 and ten combined design lenses 10 for correction of a spherical aberration. In some embodiments, lens 10 may be used to correct an aberration, such as a Z42 aberration. Lens 10 may have an associated aperture, such as a 4.5 mm IOL aperture. As depicted in FIG. 11, a Z42 aberration may be between about 0.74 microns and about 0.92 microns, with a nominal spherical aberration of about 0.83 microns. Embodiments of separated design aspheric toric IOLs 10 disclosed herein may correct a Z42 spherical aberration from about 0.74 microns up to about 0.81 microns, based on a sample population of ten lenses 10 sampled from a population of about 100 IOLs 10. Embodiments of combined design aspheric toric IOLs 10 disclosed herein may correct a Z42 spherical aberration from about 0.79 microns up to about 0.85 microns, based on a sample population of ten lenses sampled from a population of about 100 IOLs.

Embodiments disclosed herein may be useful for correcting or mitigating corneal astigmatism.

Figure 12:
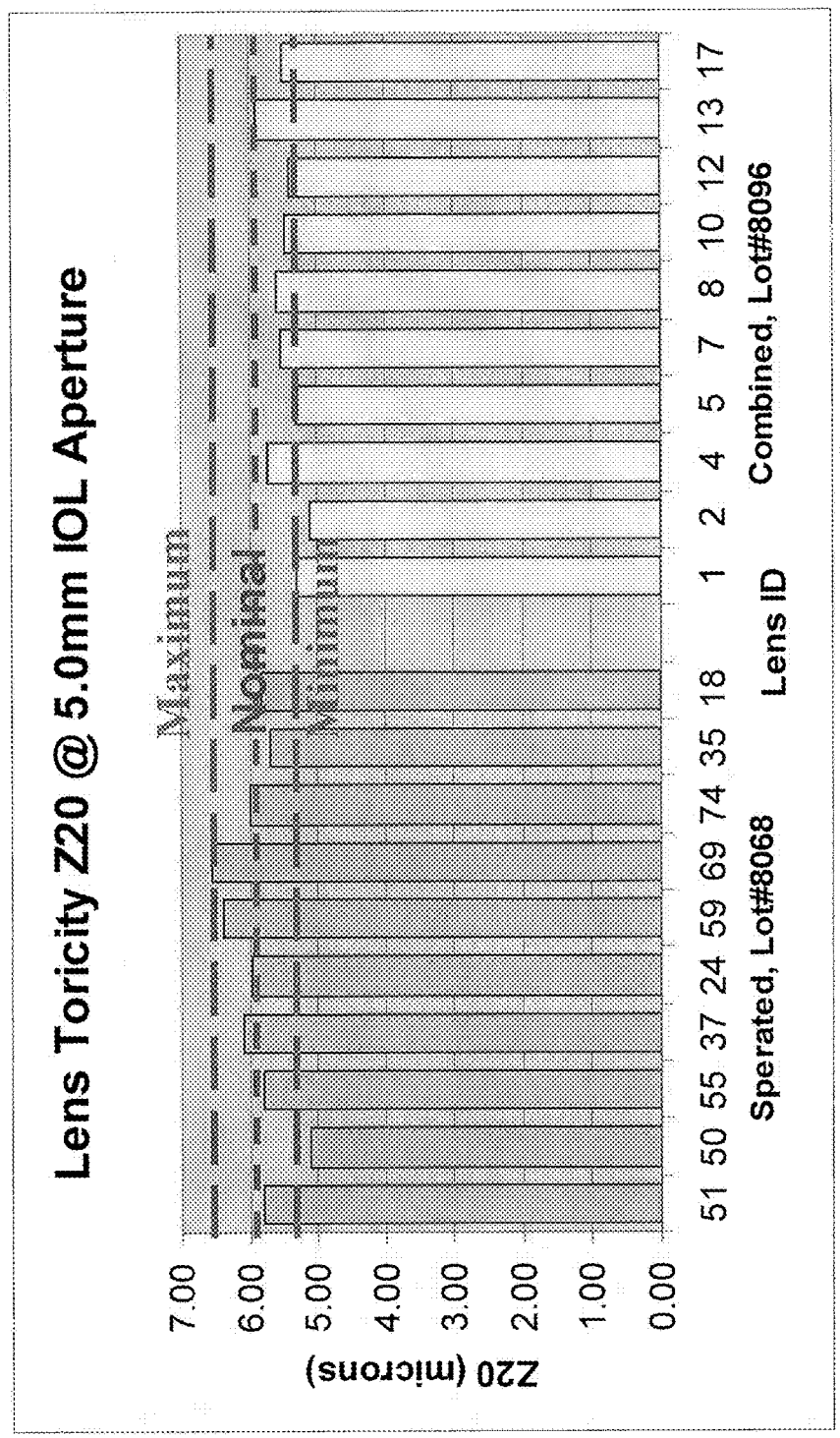
FIG. 12 is a graphical comparison of the lens toricity of ten separated design lenses and ten combined design lenses for correction of an astigmatism.

FIG. 12 depicts a graphical comparison of the lens toricity of ten separated design lenses 10 and ten combined design lenses 10 for correction of a Z20 astigmatism. In some embodiments, a Z20 astigmatism may be associated with a 5.0 mm IOL aperture. As depicted in FIG. 12, a Z20 astigmatism may be between about 5.3 microns and about 6.5 microns, with a nominal astigmatism of about 5.9 microns. Embodiments of separated design aspheric toric IOLs 10 disclosed herein may correct a Z20 astigmatism from about 5.1 microns up to about 6.5 microns, based on a sample population of ten lenses 10 sampled from a population of about 100 IOLs 10. Embodiments of combined design aspheric toric IOLs 10 disclosed herein may correct a Z20 astigmatism from about 5.1 microns up to about 5.9 microns, based on a sample population of ten lenses 10 sampled from a population of about 100 IOLs 10.

Figure 13:
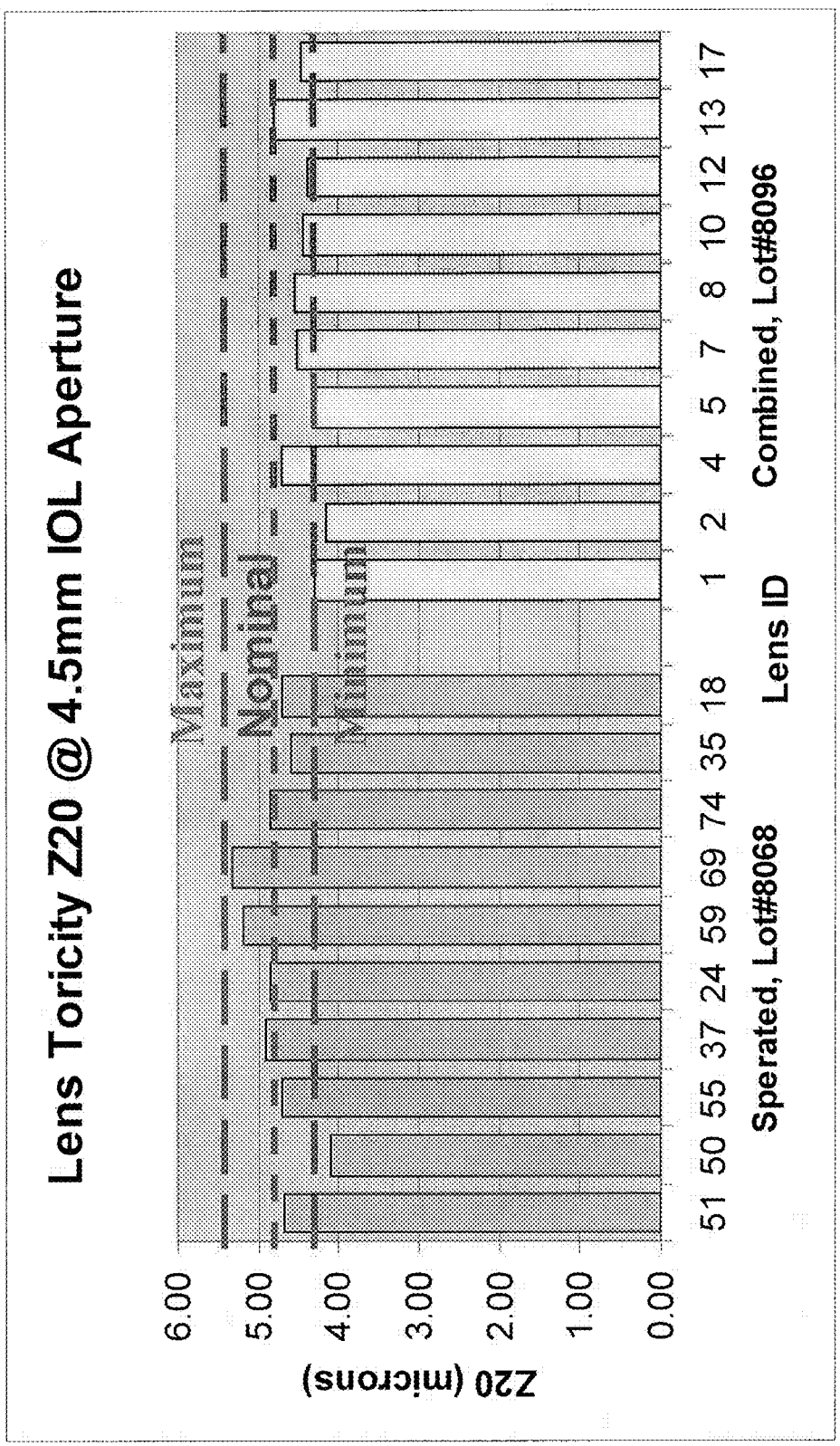
FIG. 13 is a graphical comparison of the lens toricity of ten separated design lenses and ten combined design lenses for correction of an astigmatism.

FIG. 13 depicts a graphical comparison of the lens toricity of ten separated design lenses 10 and ten combined design lenses 10 for correction of a Z20 astigmatism at a 4.5 mm IOL aperture. As depicted in FIG. 13, a Z20 astigmatism may be between about 4.3 microns and about 5.3 microns, with a nominal astigmatism of about 4.8 microns. Embodiments of separated design aspheric toric IOLs 10 disclosed herein may correct a Z20 astigmatism from about 4.1 microns up to about 5.4 microns, based on a sample population of ten lenses 10 sampled from a population of about 100 IOLs 10. Embodiments of combined design aspheric toric IOLs 10 disclosed herein may correct a Z20 astigmatism from about 4.1 microns up to about 4.8 microns, based on a sample population of ten lenses 10 sampled from a population of about 100 IOLs 10.

Figure 14:
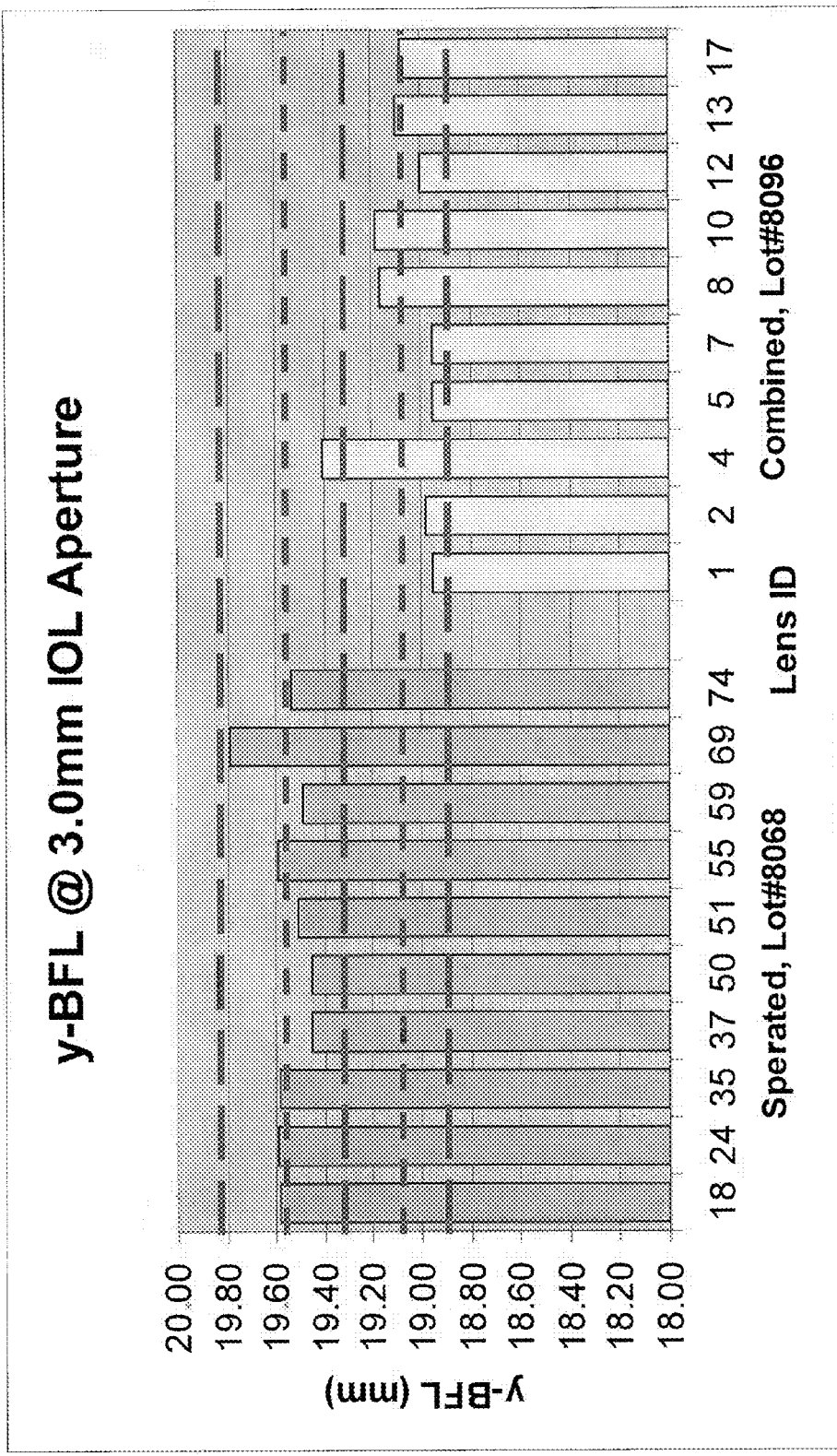
FIG. 14 is a graphical comparison of the lens Back Focal Length (BFL) of ten separated design lenses and ten combined design lenses.

FIG. 14 depicts a graphical comparison of the lens Back Focal Length (BFL) of ten separated design lenses 10 and ten combined design lenses 10 for a 3.0 mm IOL aperture. A first y-BFL for a 21.0 D aspheric toric IOL 10 may be between about 19.30 mm and about 19.82 mm, with a nominal y-BFL of about 19.59 microns. As depicted in FIG. 14, the y-BFL for several aspheric toric IOLs 10 having a separated design may result in lens 10 having an optical power close to 21.0 D. As depicted in FIG. 14, a y-BFL for a 21.5 D may be between about 18.90 mm and about 19.30 mm, with a nominal y-BFL of about 19.10 microns. As depicted in FIG. 14, the x-BFL for several aspheric toric IOLs 10 having a combined design may result in lens 10 having an optical power close to 21.5 D.

Figure 15:
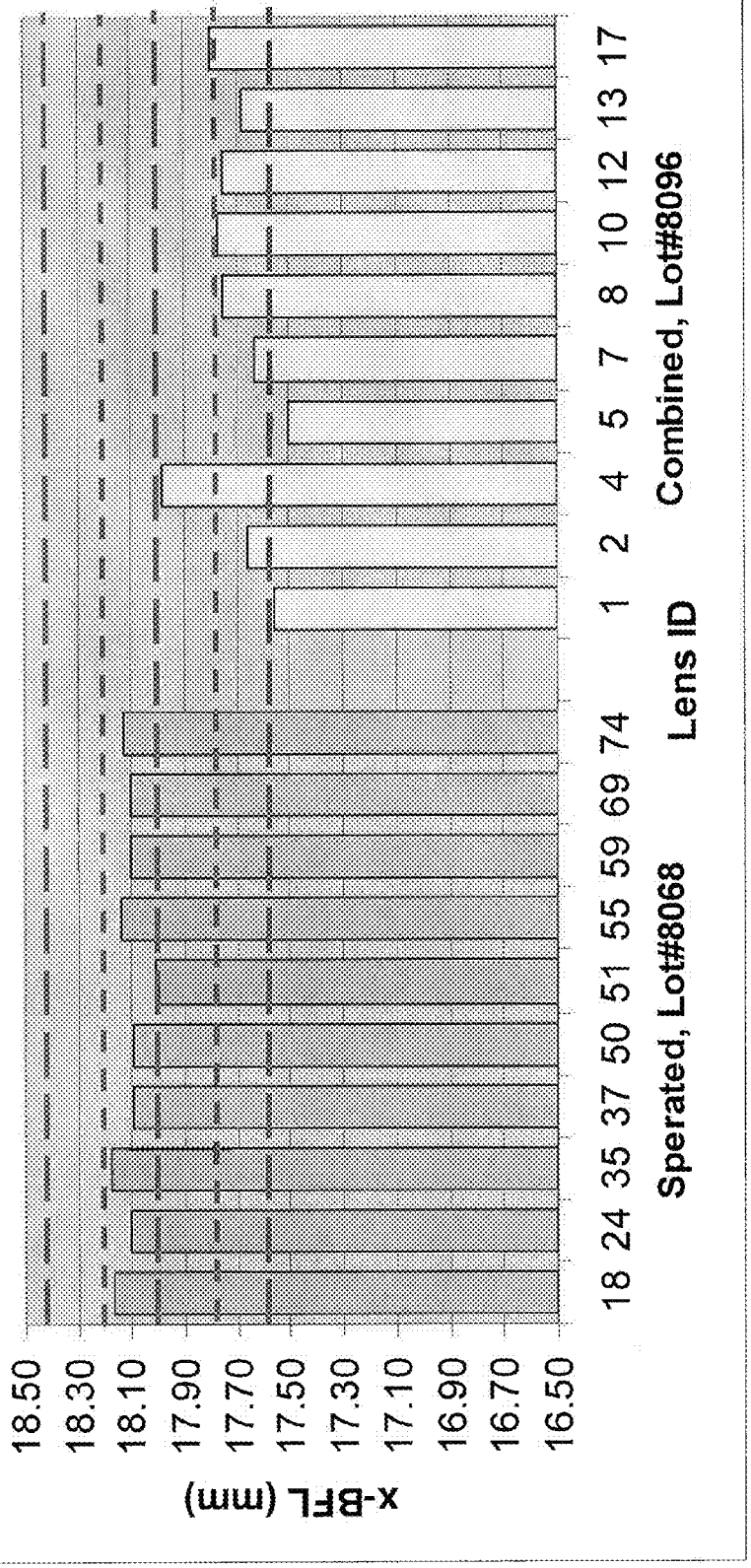
FIG. 15 is a graphical comparison of the lens Back Focal Length (BFL) of ten separated design lenses and ten combined design lenses.

FIG. 15 depicts a graphical comparison of the lens Back Focal Length (BFL) of ten separated design lenses 10 and ten combined design lenses 10 for a 3.0 mm IOL aperture. A first x-BFL for a 21.0 D aspheric toric IOL 10 may be between about 18.00 mm and about 18.40 mm, with a nominal x-BFL of about 18.20 microns. As depicted in FIG. 15, the x-BFL for several aspheric toric IOLs 10 having a separated design may result in lens 10 having an optical power close to 21.0 D. As depicted in FIG. 15, a x-BFL for a 21.5 D may be between about 17.60 mm and about 18.00 mm, with a nominal x-BFL of about 18.00 microns. As depicted in FIG. 15, the x-BFL for several aspheric toric IOLs 10 having a combined design may result in lens 10 having an optical power close to 21.5 D.

Figure 16:
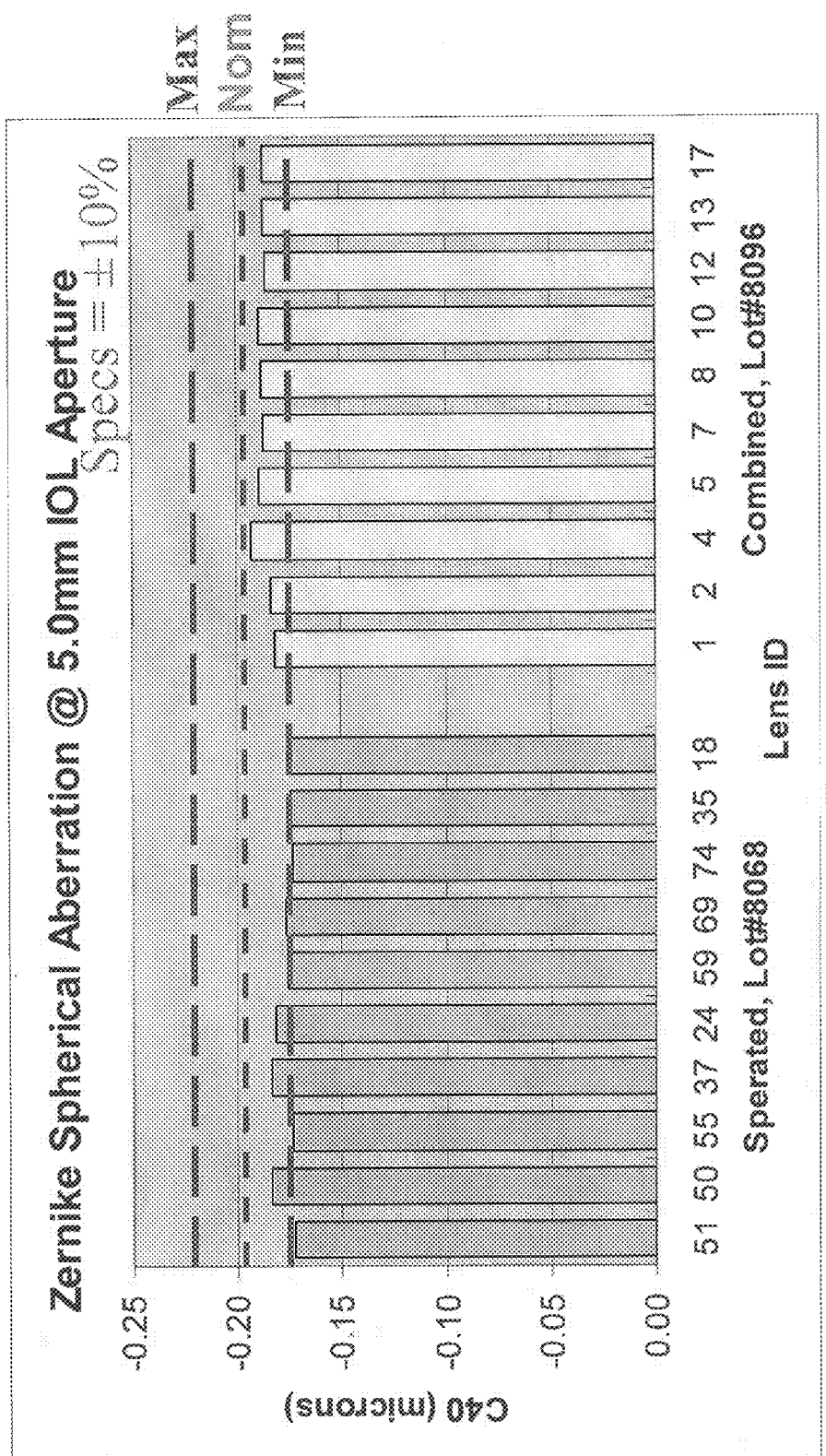
FIG. 16 depicts a graphical comparison of the lens spherical aberration (SA) of ten separated design lenses and ten combined design lenses according to one embodiment.

FIG. 16 depicts a graphical comparison of the lens spherical aberration (SA) of ten separated design lenses 10 and ten combined design lenses 10 for a 5.0 mm IOL aperture. As depicted in FIG. 16, a Zernike spherical aberration (C40) may have a minimum aberration of −0.17 microns and a maximum aberration of −0.23 microns, with a nominal aberration of −0.19 microns. The range of correction provided by IOLs 10 utilizing a separated design may lie between −0.17 microns to about −0.18 microns. A range of correction provided by IOLs 10 utilizing a combined design may lie between approximately −0.18 and −0.19 microns.

Figure 17:
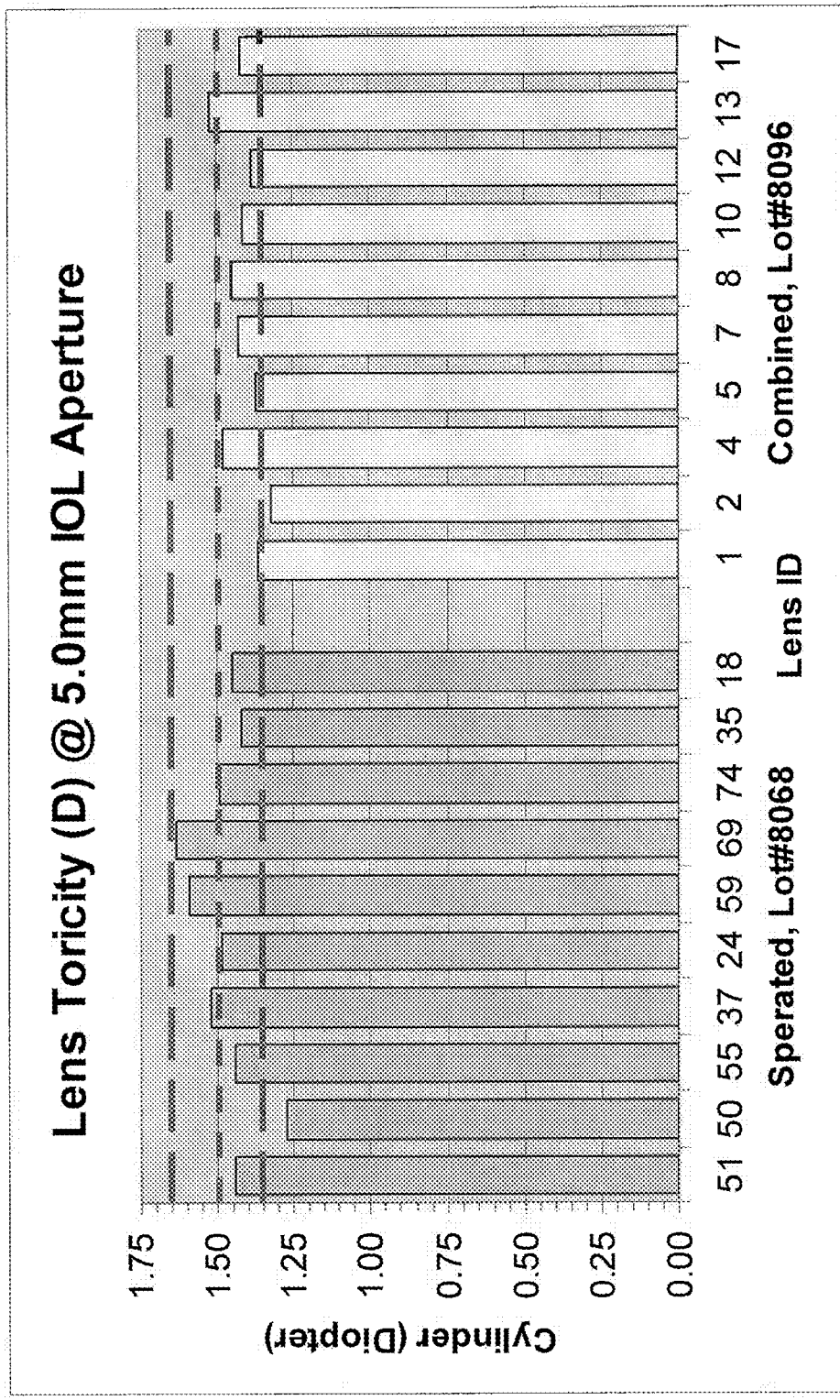
FIG. 17 depicts a graphical comparison of the lens toricity of ten separated design lenses and ten combined design lenses according to one embodiment.

FIG. 17 depicts a graphical comparison of the lens toricity of ten separated design lenses 10 and ten combined design lenses 10 for a 5.0 mm IOL aperture. As depicted in FIG. 17, a cylinder (Diopter) may have a minimum cylinder of 1.30 D and a maximum cylinder of 1.65 D, with a nominal cylinder of 1.5 D. The range of correction provided by IOLs 10 utilizing a separated design may lie between 1.25 D to about 1.75 D. A range of correction provided by IOLs 10 utilizing a combined design may lie between approximately 1.2 D and 1.6 D.

Figure 18:
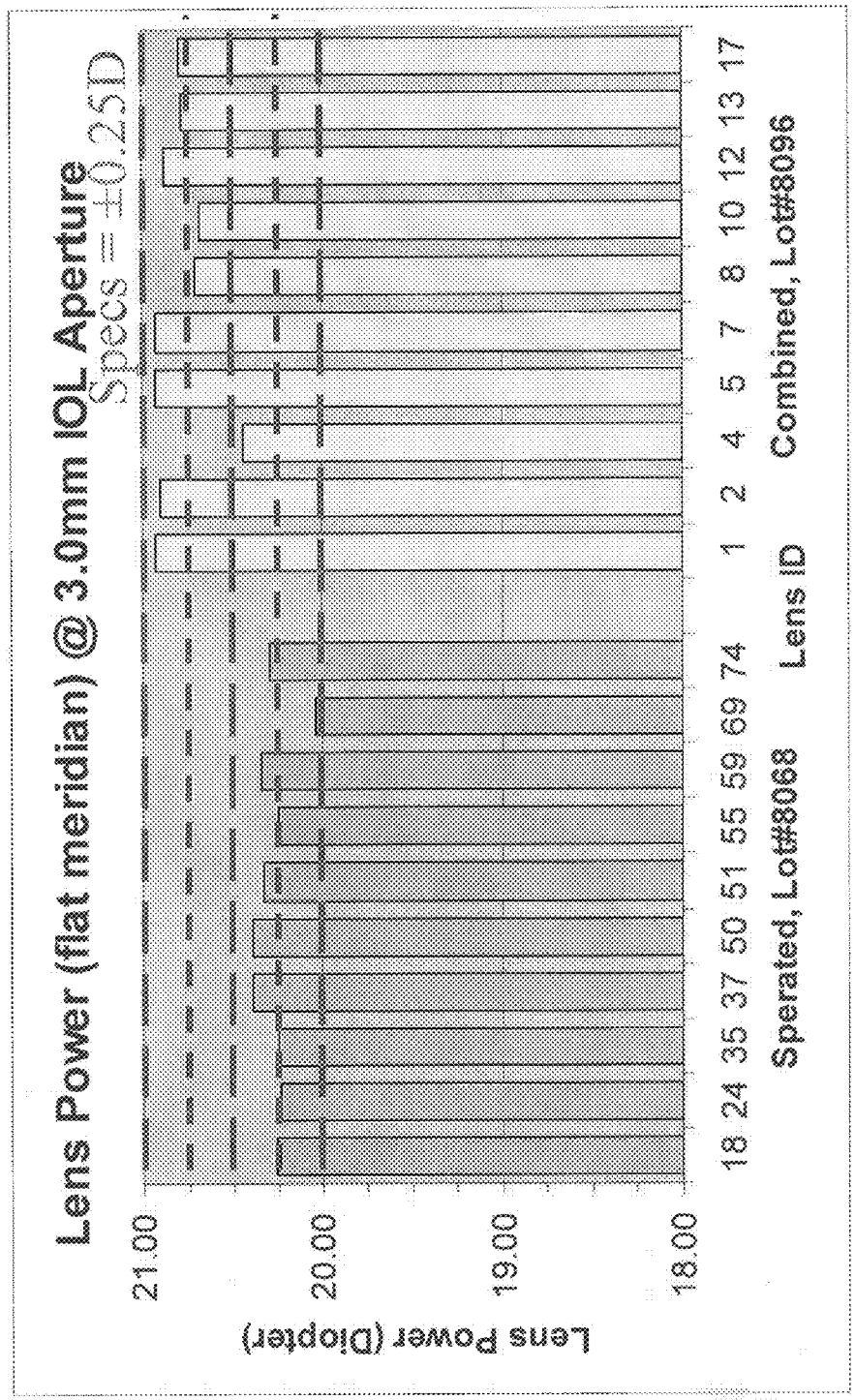
FIG. 18 depicts a graphical comparison of lens power of ten separated design lenses and ten combined design lenses according to one embodiment.

FIG. 18 depicts a graphical comparison of lens power of ten separated design lenses 10 and ten combined design lenses 10 for a 3.0 mm IOL aperture. As depicted in FIG. 18, lens power (flat meridian) between 20.00 and 20.50 D may provide SE of 21.0 D and lens power (flat meridian) between 20.6 D and 21.0 D may provide SE of 21.5 D. A range of correction provided by IOLs 10 utilizing a separated design may lie between approximately 20.00 and 20.40 D. For example, lens 10 identified as '18' may provide lens power of approximately 20.25 D. A range of correction provided by IOLs 10 utilizing a combined design may lie between approximately 20.40 and 20.90 D. For example, lens 10 identified as '1' may provide lens power of approximately 20.90 D.

Figure 19:
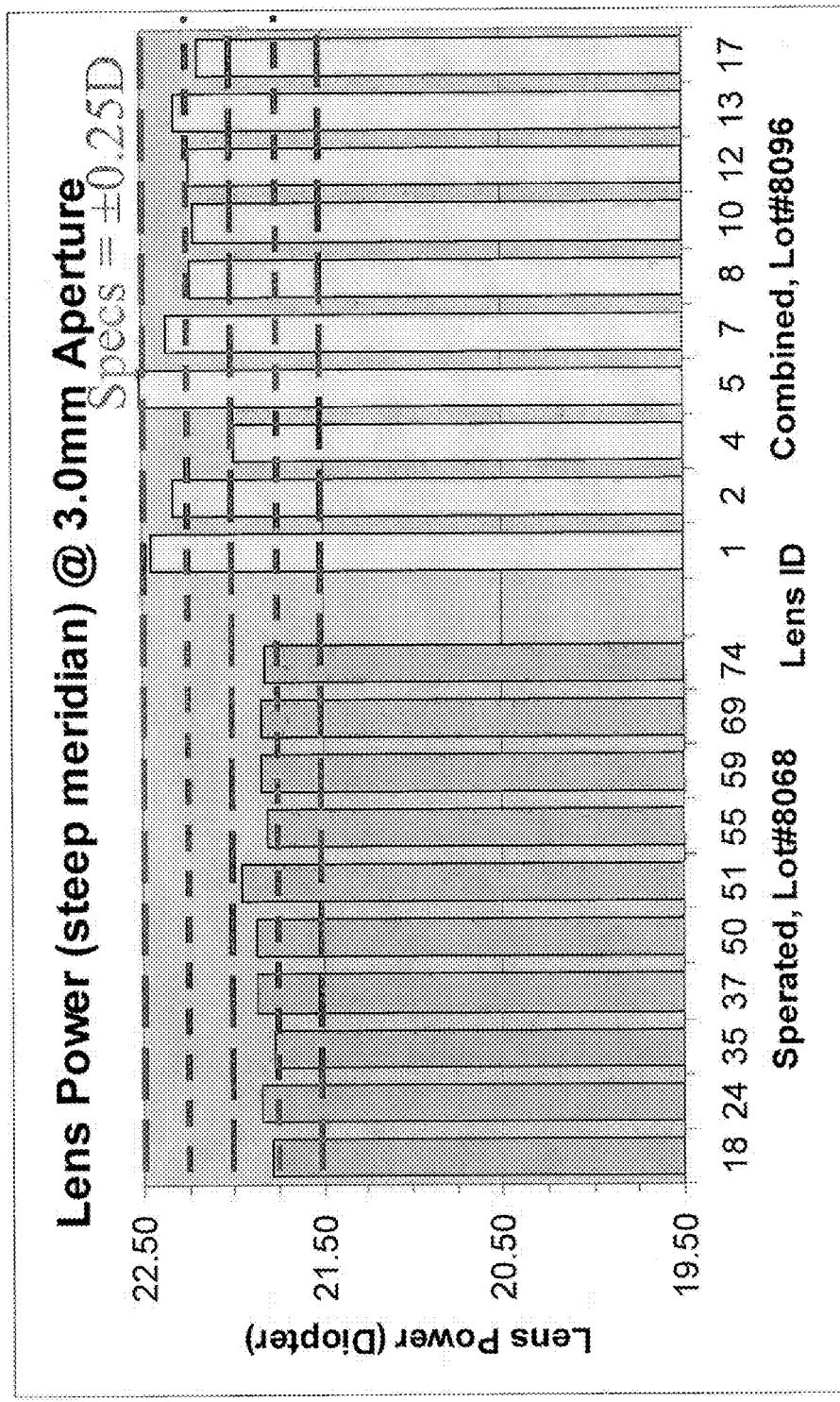
FIG. 19 depicts a graphical representation of lens power at a steep meridian according to one embodiment.

FIG. 19 depicts a graphical representation of lens power at a steep meridian for a 3.0 mm aperture with toric bench. As depicted in FIG. 21, lens power (steep meridian) between 21.50 and 22.00 D may provide SE of 21.0 D and lens power (steep meridian) between 22.00 D and 22.50 D may provide SE of 21.5 D. A range of correction provided by IOLs 10 utilizing a separated design may lie between approximately 21.75 and 21.90 D. For example, lens 10 identified as '18' may provide lens power of approximately 20.25 D. A range of correction provided by IOLs 10 utilizing a combined design may lie between approximately 22.00 and 20.90 D. For example, lens 10 identified as '1' may provide lens power of approximately 20.90 D.

TABLE 1

| | Asphericity/Toricity separated on two surfaces | Asphericity/Toricity combined on same surface |
|---|---|---|
| Optical Power Anterior | 21D/T3 (1.5D cyl) | 21D/T3 (1.5D cyl) |
| Radius | 19.613 mm | 19.609 |
| Conic | −36.211 | |
| Posterior (bi-conic) | | |
| Radius X | −23.808 mm | −23.814 mm |
| Conic X | | −65.571 |
| Radius Y | −20.446 mm | −20.451 mm |
| Conic Y | | −42.168 |
| Center Thickness | 0.611 mm | 0.612 mm |
| Edge Thickness (@ 45 degrees) | 0.21 mm | 0.21 mm |

Table 1 depicts various sample results of two embodiments of aspheric/toric lenses 10. For the embodiments depicted in Table 1, the optical power and edge thickness of the separated design embodiments equaled the combined design embodiments, and the center thickness was nearly the same.

Figure 20:
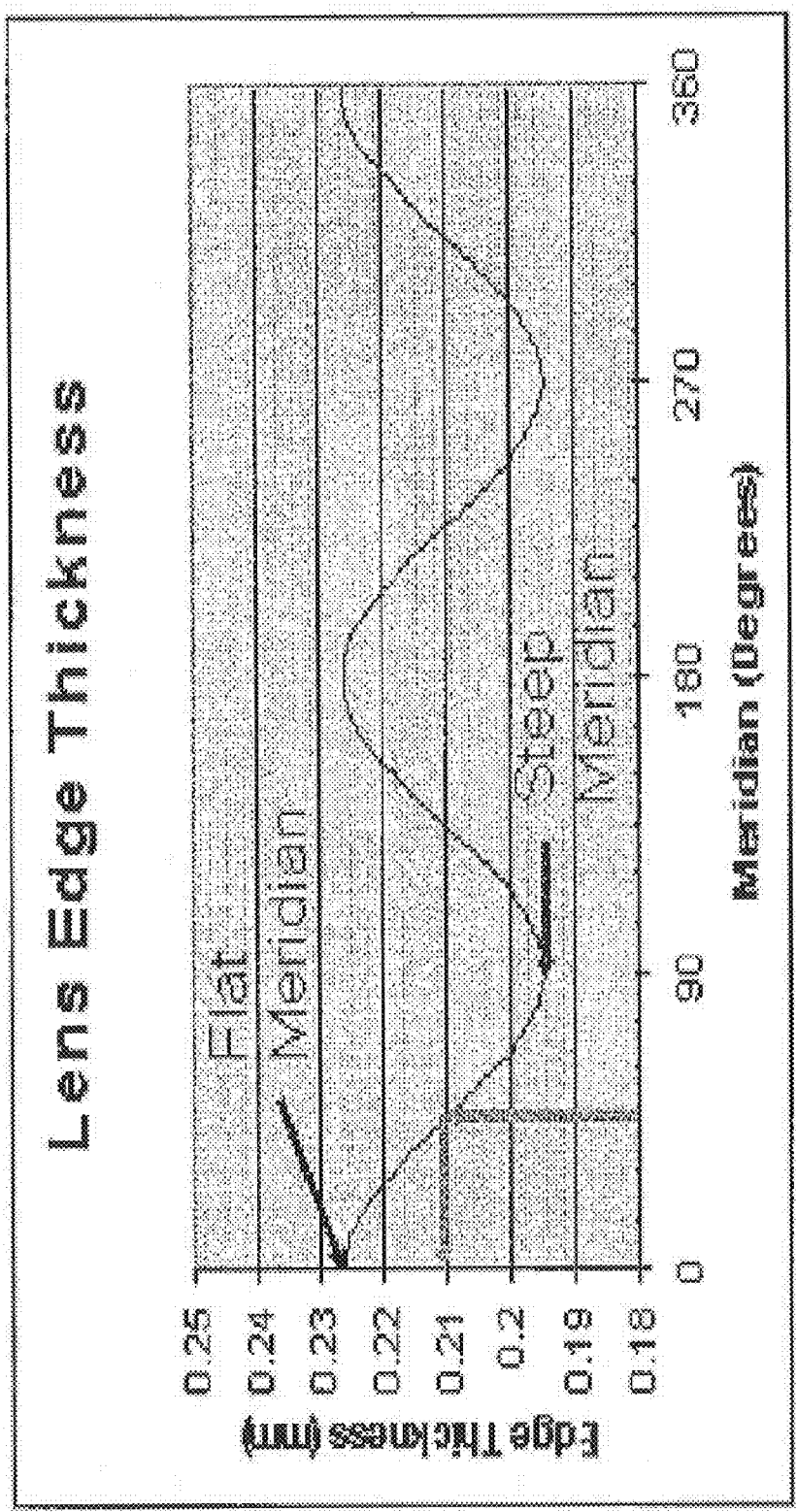
FIG. 20 depicts a graphical representation of the edge thickness according to one embodiment.

In some embodiments, the thickness of the edge of lens 10 may vary. In some embodiments, the thickness of the edge of lens 10 may vary periodically. In some embodiments, variation in the edge thickness may be sinusoidal. In some embodiments, the thickness of the edge of lens 10 may be equal at 45 degree meridians. An advantage to having equal edge thickness at the 45 degree meridians may be the ability to use existing tools to implant lens 10 into an eye. FIG. 20 depicts a graphical representation of the edge thickness for one embodiment of aspheric toric intraocular lens 10. As depicted in FIG. 20, the variation in thickness may be sinusoidal. In some embodiments, a sinusoidal variation may result in the lens thickness being equal at a meridian. In some embodiments, the lens thickness may be equal at the four 45-degree meridians and may be a maximum or minimum thickness at the steep and/or flat meridians. As depicted in FIG. 20, the lens thickness is a maximum (i.e., approximately 0.225 mm) at the flat meridian and a minimum (i.e., approximately 0.195 mm) and equal (i.e., approximately 0.21 mm) at the four 45-degree meridians.

In accordance with the foregoing, methods and apparatus for providing toricity and asphericity on a single lens 10 have been provided. More particularly, improved IOLs have been disclosed that achieve excellent distance and near vision without the need for additional visual correction (e.g., spectacles). Thus, the foregoing embodiments allow the natural crystalline lens to be replaced with an IOL that provides excellent vision over a range of object distances.

During a surgical procedure, various embodiments of IOLs described above can be implanted using known surgical tools and techniques. According to various embodiments, lenses can be used to support Astigmatic correction strategies for enhancing vision such as, but not limited to, minimizing residual astigmatism of the whole eye, maintaining preoperative cylinder axis, or optimizing residual astigmatism at preferable meridians. During a procedure the surgeon can use markings on the lens (such as markings 22 of FIG. 1) to properly align the toric shape of the lens with the meridians of the astigmatism.

Although embodiments have been described in detail herein, it should be understood that the description is by way of example only and is not to be construed in a limiting sense.

It is to be further understood, therefore, that numerous changes in the details of the embodiments and additional embodiments will be apparent, and may be made by, persons of ordinary skill in the art having reference to this description. It is contemplated that all such changes and additional embodiments are within scope of the claims below.

What is claimed is:

1. An ophthalmic device, comprising:
an ophthalmic lens having an anterior surface and a posterior surface; and
one or more haptics coupled to the ophthalmic lens;
wherein one of the posterior or anterior surfaces is shaped so that the ophthalmic lens is configured as an aspheric lens and one of the posterior or anterior surfaces is shaped so that the ophthalmic lens is configured as a toric lens, wherein the ophthalmic lens has a selected edge thickness that varies periodically around the ophthalmic lens, and wherein the selected edge thickness is equal at 45 degree meridians of the ophthalmic lens and is between 0.2 and 0.3 mm at the 45 degree meridians.

2. The ophthalmic device of claim 1, wherein the posterior surface is shaped so that the ophthalmic lens is configured as the aspheric lens and the toric lens.

3. The ophthalmic device of claim 1, wherein the anterior surface is shaped so that the ophthalmic lens is configured as the aspheric lens and the toric lens.

4. The ophthalmic device of claim 1, wherein the posterior surface is shaped so that the ophthalmic lens is configured as an aspheric lens and the anterior surface is shaped so that the ophthalmic lens is configured as a toric lens.

5. The ophthalmic device of claim 1, wherein the anterior surface is shaped so that the ophthalmic lens is configured as an aspheric lens and the posterior surface is shaped so that the ophthalmic lens is configured as a toric lens.

6. The ophthalmic device of claim 1, wherein the aspheric surface is shaped with a single asphericity for all cylinder meridians.

7. The ophthalmic device of claim 1, wherein the aspheric surface is shaped with a first asphericity for a first meridian and a second asphericity for a second meridian.

8. The ophthalmic device of claim 1, wherein the first and second meridians are the principle meridians.

9. The ophthalmic device of claim 1, wherein the haptics are roughened to promote adherence with biological material.

10. The ophthalmic device of claim 1, wherein the ophthalmic device comprises a set of markers placed to aid alignment of the ophthalmic lens relative to one or more meridians of an astigmatism.

11. An ophthalmic lens comprising:
an anterior surface; and
a posterior surface
one of the anterior or posterior surface having asphericity and one of the anterior or posterior surface having toricity, wherein the ophthalmic lens has a selected edge thickness that varies periodically around the ophthalmic lens, and wherein the selected edge thickness is equal at 45 degree meridians of the ophthalmic lens and is between 0.2 and 0.3 mm at the 45 degree meridians.

12. The ophthalmic lens of claim 11, wherein a single surface is shaped with asphericity and toricity.

13. The ophthalmic lens of claim 12, wherein the single surface is defined by:

$$sag_1 = \text{toric}(r, \theta),$$

wherein $$\text{toric}(R_{avg}, r, \theta) = \frac{(c_x \cos^2\theta + c_y \sin^2\theta)r^2}{1 + \sqrt{1 - (1+k_k)c_x^2 r^2 \cos^2\theta - (1+k_y)c_y^2 r^2 \sin^2\theta}},$$

wherein $c_x = \frac{1}{R_x}, c_y = \frac{1}{R_y}$

14. The ophthalmic lens of claim 11, wherein one of the anterior surface and the posterior surface has the toricity and the other has the asphericity.

15. The ophthalmic lens of claim 14, wherein the toric surface and the aspheric surface are defined respectively by:

$$sag_1 = \text{toric}(r, \theta) \text{ and } sag_2 = asph(r),$$

wherein: $\text{toric}(r, \theta) = \frac{(c_x \cos^2\theta + c_y \sin^2\theta)r^2}{1 + \sqrt{1 - (1+k_x x)c_x^2 r^2 \cos^2\theta - (1+k_y)c_y^2 r^2 \sin^2\theta}},$ and $c_x = \frac{1}{R_{1x}}, c_y = \frac{1}{R_{1y}}$ and $$asph(r) = \frac{cr^2}{1 + \sqrt{1 - (1+k)c^2 r^2}}, c = \frac{1}{R_2}.$$

* * * * *